United States Patent
Shigemori et al.

(12)

(10) Patent No.: US 9,655,500 B2
(45) Date of Patent: May 23, 2017

(54) RECEIVING DEVICE

(75) Inventors: Toshiaki Shigemori, Hachioji (JP);
Seiichiro Kimoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 2166 days.

(21) Appl. No.: 12/691,242

(22) Filed: Jan. 21, 2010

(65) Prior Publication Data

US 2010/0130820 A1 May 27, 2010

Related U.S. Application Data

(63) Continuation of application No. PCT/JP2008/063027, filed on Jul. 18, 2008.

(30) Foreign Application Priority Data

Jul. 24, 2007 (JP) .................................. 2007-192243

(51) Int. Cl.
*A61B 1/04* (2006.01)
*H04B 7/00* (2006.01)
(Continued)

(52) U.S. Cl.
CPC .......... *A61B 1/041* (2013.01); *A61B 1/00016* (2013.01); *A61B 5/073* (2013.01);
(Continued)

(58) Field of Classification Search
USPC .......... 607/60; 600/103, 109, 117, 118, 160; 370/278, 279, 315; 455/73, 41.2
See application file for complete search history.

(56) References Cited

U.S. PATENT DOCUMENTS 5,260,944 A * 11/1993 Tomabechi .................. 370/347
6,757,523 B2    6/2004 Fry
(Continued)

FOREIGN PATENT DOCUMENTS

EP    1 810 607 A1    7/2007
EP    1 967 124 A1    9/2008
(Continued)

OTHER PUBLICATIONS

Japanese Office Action dated Feb. 19, 2013 from corresponding Japanese Patent Application No. 2007-192243 together with an English language translation.
(Continued)

*Primary Examiner* — Matthew J Kasztejna
*Assistant Examiner* — Aaron B Fairchild
(74) *Attorney, Agent, or Firm* — Scully, Scott, Murphy & Presser, P.C.

(57) ABSTRACT

A receiving device includes a receiving unit that receives, via a receiving antenna, an image signal including an in-vivo image of a subject that is captured by an in-vivo-image acquiring device introduced into the subject; a transmitting unit that wirelessly transmits the image signal to a real-time display device that displays the in-vivo image in real time; a detecting unit that detects a non-receiving period in which the receiving unit does not receive the image signal; and a control unit that performs a control to wirelessly transmit the image signal to the real-time display device during the non-receiving period immediately after receipt of the image signal by the receiving unit.

8 Claims, 14 Drawing Sheets

(51) Int. Cl.
- *H04B 1/38* (2015.01)
- *H04B 1/44* (2006.01)
- *A61B 1/00* (2006.01)
- *A61B 5/07* (2006.01)
- *H04B 1/48* (2006.01)
- *H04B 7/204* (2006.01)
- *H04B 7/212* (2006.01)
- *H04B 7/26* (2006.01)
- *A61B 5/00* (2006.01)

(52) U.S. Cl.
CPC ............ *H04B 1/44* (2013.01); *A61B 1/00036* (2013.01); *A61B 5/7232* (2013.01); *H04B 7/2043* (2013.01); *H04B 7/212* (2013.01); *H04B 7/2123* (2013.01); *H04B 7/2643* (2013.01); *H04B 2001/485* (2013.01)

(56) References Cited

U.S. PATENT DOCUMENTS

| | | | |
|---|---|---|---|
| 7,618,366 | B2 | 11/2009 | Glukhovsky et al. |
| 2005/0171418 | A1* | 8/2005 | Lin ................................ 600/407 |
| 2005/0195785 | A1 | 9/2005 | Matsumoto et al. |
| 2007/0057828 | A1 | 3/2007 | Kimura |
| 2007/0118018 | A1* | 5/2007 | Gilad et al. ................... 600/160 |
| 2007/0167715 | A1 | 7/2007 | Shigemori |
| 2008/0249360 | A1 | 10/2008 | Li et al. |

FOREIGN PATENT DOCUMENTS

| | | |
|---|---|---|
| JP | 2003-019111 | 1/2003 |
| JP | 2004-129231 | 4/2004 |
| JP | 2005-21516 A | 1/2005 |
| JP | 2005-066096 | 3/2005 |
| JP | 2005-192701 A | 7/2005 |
| JP | 2005-252718 | 9/2005 |
| JP | 2006-055431 | 3/2006 |
| JP | 2006-075365 | 3/2006 |
| JP | 2007-036577 | 2/2007 |
| JP | 2007-104635 | 4/2007 |
| JP | 2007-151809 | 6/2007 |
| JP | 2007-167555 | 7/2007 |
| JP | 2007-175188 | 7/2007 |
| JP | 2007-180927 | 7/2007 |
| JP | 2007-523703 A | 8/2007 |
| WO | 2006/059331 A2 | 6/2006 |
| WO | 2007/060659 A2 | 5/2007 |
| WO | WO 2007/074712 A1 | 7/2007 |
| WO | WO 2007/074887 A1 | 7/2007 |

OTHER PUBLICATIONS

International Search Report dated Aug. 19, 2008.
Japanese Office Action dated Jul. 16, 2013 issued in Japanese Patent Application No. 2007-192243.
Extended Supplementary European Search Report dated Sep. 15, 2014 from related European Application No. 08 79 1336.4.

* cited by examiner

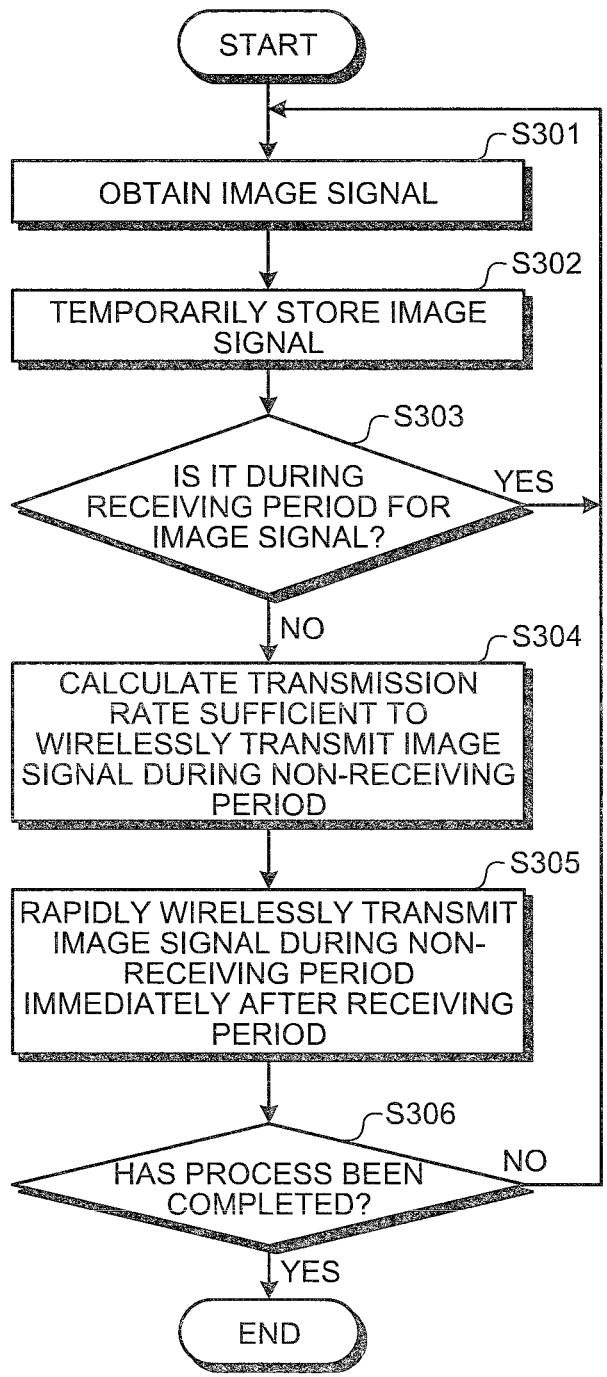

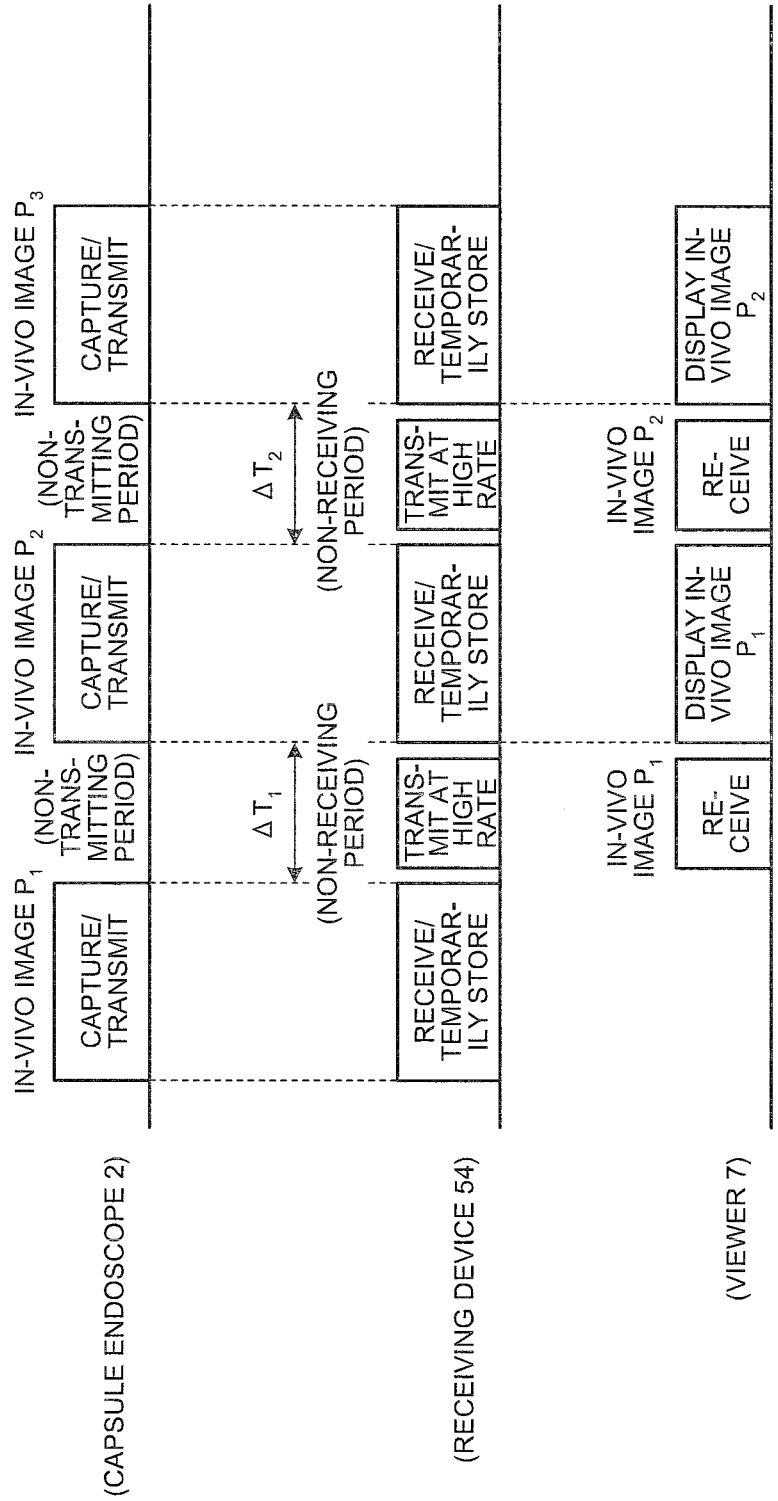

RECEIVING DEVICE

CROSS-REFERENCE TO RELATED APPLICATIONS

This application is a continuation of PCT international application Ser. No. PCT/JP2008/063027 filed on Jul. 18, 2008 which designates the United States, incorporated herein by reference, and which claims the benefit of priority from Japanese Patent Applications No. 2007-192243, filed on Jul. 24, 2007, incorporated herein by reference.

BACKGROUND OF THE INVENTION

1. Field of the Invention

The present invention relates to a receiving device that receives image signals wirelessly transmitted by an in-vivo-image acquiring device that is introduced into a subject, such as a patient, to capture images of insides of organs of the subject.

2. Description of the Related Art

In the field of endoscopes, a capsule endoscope having an imaging function and a wireless communicating function included in a capsule-shaped casing has recently arrived on the market as an in-vivo-image acquiring device that obtains images of insides of a living body. After being swallowed through a mouth of a subject such as a patient for observation (examination), the capsule endoscope is moved by a peristaltic motion and the like in organs such as a stomach and a small intestine, and successively captures images of insides of the organs (hereinafter, also "in-vivo image") of the subject at specific time intervals until the capsule endoscope is spontaneously excreted from the subject. The capsule endoscope successively wirelessly transmits image signals including these in-vivo images to outside.

The image signals wirelessly transmitted by the capsule endoscope are successively received by a receiving device carried by the subject. The receiving device receives the image signals from the capsule endoscope within the subject via a specific wave, and obtains the in-vivo images included in the received image signals. The receiving device has a recording medium removably attached thereto, and records a group of in-vivo images of the subject obtained (received) in this way in the recording medium. The recording medium having the group of in-vivo images of the subject recorded therein is then detached from the receiving device and inserted into an image display device. The image display device obtains the group of in-vivo images of the subject via the recording medium, and displays the obtained group of in-vivo images of the subject on a display. A user such as a doctor or a nurse successively observes the in-vivo images of the subject displayed by the image display device, and examines the insides of the organs of the subject through the in-vivo images (for example, see Japanese Laid-open Patent Publication No. 2003-19111).

Meanwhile, the receiving device is not limited to the one that transfers the group of in-vivo images of the subject to the image display device via the recording medium. Another receiving device that is communicably connected via a cable to a real-time display device that displays in-vivo images of a subject in real time, thereby to transmit the in-vivo images to the real-time display device via the cable in real time is known. In this example, the real-time display device displays the in-vivo images received from a capsule endoscope within the subject by the receiving device in real time. Still another receiving device that includes a wireless transmitting unit that wirelessly transmits a group of in-vivo images of a subject to outside, thereby to wirelessly transmit the group of in-vivo images received from a capsule endoscope within the subject to the image display device described above is known (for example, see Japanese Laid-open Patent Publication No. 2005-66096).

The receiving device described above can include a wireless transmitting unit that wirelessly transmits image signals to the real-time display device, instead of transmitting the in-vivo images to the real-time display device via the cable. This enables the receiving device to wirelessly transmit the image signals (the in-vivo images of the subject) received from the capsule endoscope within the subject to the real-time display device in real time, thereby enhancing usability of the real-time display device. Specifically, botheration of a need to connect the real-time display device and the receiving device with the cable to enable the real-time display device to display the in-vivo images, inconvenience of a limited accessible range of a user such as a doctor or a nurse that observes the in-vivo images displayed by the real-time display device due to the cable, and the like can be eliminated.

SUMMARY OF THE INVENTION

A receiving device according to an aspect of the present invention includes a receiving unit that receives, via a receiving antenna, an image signal including an in-vivo image of a subject that is captured by an in-vivo-image acquiring device introduced into the subject; a transmitting unit that wirelessly transmits the image signal to a real-time display device that displays the in-vivo image in real time; a detecting unit that detects a non-receiving period in which the receiving unit does not receive the image signal; and a control unit that performs a control to wirelessly transmit the image signal to the real-time display device during the non-receiving period immediately after receipt of the image signal by the receiving unit.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 13 is a flowchart of an example of a process procedure performed by a control unit of the receiving device according to the fourth embodiment; and FIG. 14 is a schematic diagram of an example of a sequential control in a receiving device that wirelessly transmits an image signal to a viewer based on a transmission rate increased according to a shortened non-receiving period of the receiving device.

DETAILED DESCRIPTION OF THE PREFERRED EMBODIMENTS

As described previously, a receiving device including a wireless transmitting function for the real-time display device receives the image signal wirelessly transmitted by the capsule endoscope within the subject via a receiving antenna. Accordingly, when wirelessly transmitting the image signal received from the capsule endoscope to the real-time display device in real time, the receiving device may cause interference between the image signal wirelessly transmitted and the image signal received via the receiving antenna. This prohibits reception of the image signal from the capsule endoscope.

To solve the problems related to the receiving device, it is conceivable that different frequency bands are used for the image signal received by the receiving device from the capsule endoscope via the receiving antenna and for the image signal wirelessly transmitted by the receiving device to the real-time display device. In this way, the reception and the transmission of the image signals in the different frequency bands can be achieved during the same time period. However, this causes other problems. One of the problems is that power consumption of the receiving device is increased when receiving the image signal via the receiving antenna and wirelessly transmitting the image signal in the different frequency band to the real-time display device during the same time period. Another problem is that the receiving device is increased in size because a shield for preventing electromagnetic interference in the casing of the receiving device is needed even when the frequencies for the image signals are different. These problems cannot be ignored in terms of a fact that the receiving device is carried by (attached to) the subject for a long time to receive a group of in-vivo images from the capsule endoscope within the subject.

Preferred embodiments of a receiving device according to the present invention will be explained below in detail with reference to the accompanying drawings. The present invention is not limited to the embodiments.

First Embodiment

Figure 1:
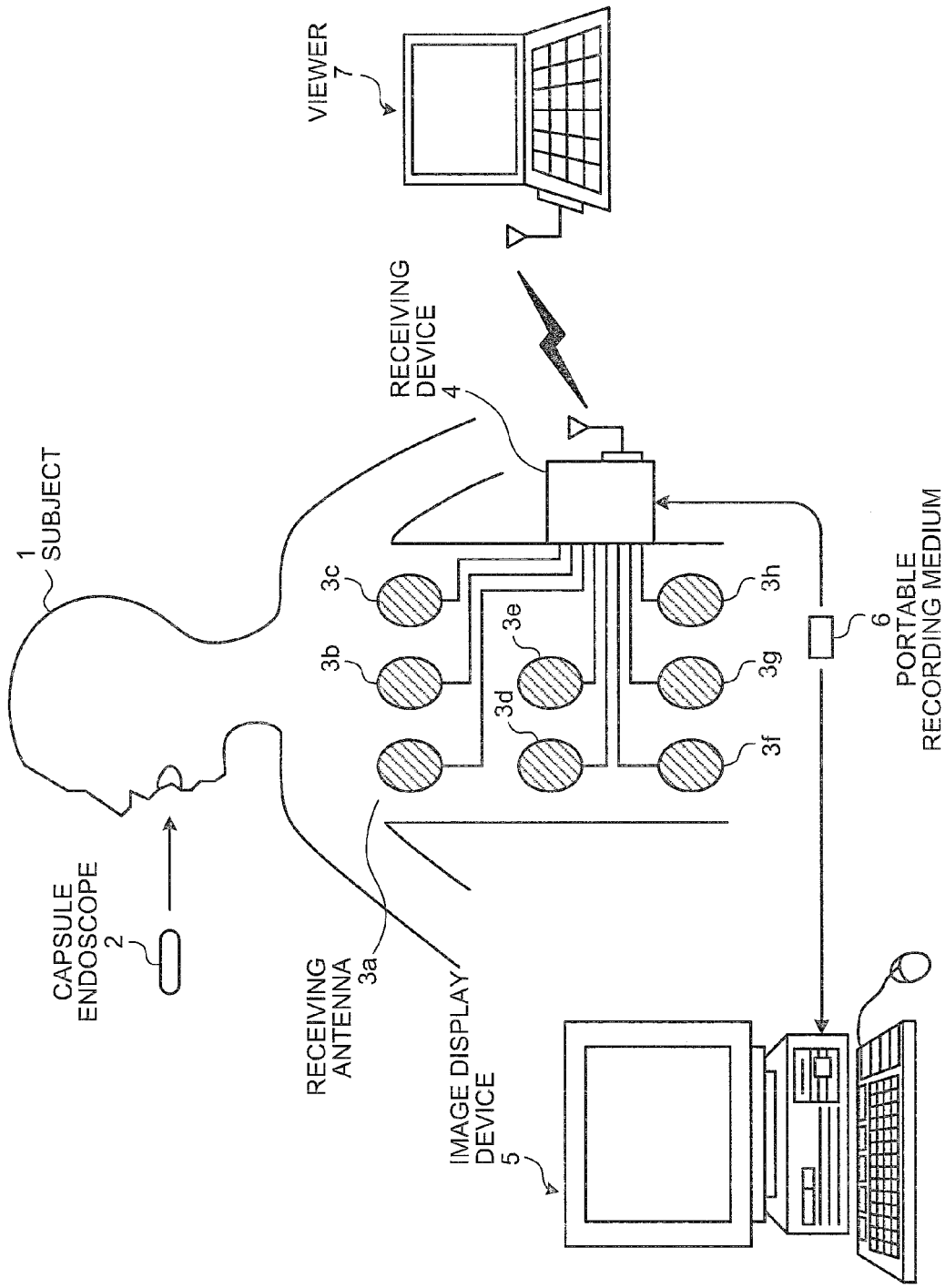
FIG. 1 is a schematic diagram of a configuration example of an in-vivo-image acquiring system according to a first embodiment of the present invention.

FIG. 1 is a schematic diagram of a configuration example of an in-vivo-image acquiring system according to a first embodiment of the present invention. As shown in FIG. 1, the in-vivo-image acquiring system according to the first embodiment includes a capsule endoscope 2, which is an example of an in-vivo-image acquiring device that captures a group of in-vivo images of a subject 1, a receiving device 4 that receives the group of in-vivo images of the subject 1 from the capsule endoscope 2 introduced into the subject, an image display device 5 that displays the group of in-vivo images of the subject 1 received by the receiving device 4 (that is, the group of in-vivo images captured by the capsule endoscope 2), a portable recording medium 6 for transfer of data between the receiving device 4 and the image display device 5, and a viewer 7 that displays the in-vivo images received by the receiving device 4 in real time.

The capsule endoscope 2 includes an imaging function and a wireless communicating function in a capsule-shaped casing, and serves as an in-vivo-image acquiring device that is introduced into the subject 1 to capture in-vivo images of the subject 1 and wirelessly transmit the in-vivo images to outside. Specifically, after being swallowed through a mouth of the subject 1, the capsule endoscope 2 successively captures in-vivo images of the subject 1 while being moved within organs of the subject 1 by peristaltic motions of the organs and the like. Upon each capture of the in-vivo image of the subject 1, the capsule endoscope 2 successively wirelessly transmits an image signal including the captured in-vivo image to the external receiving device 4 at a predetermined frame rate.

The receiving device 4 receives the group of in-vivo images of the subject 1 captured by the capsule endoscope 2 and stores therein the received group of in-vivo images. Specifically, the receiving device 4 includes a plurality of receiving antennas 3a to 3h and is attached to (carried by) the subject 1 having the capsule endoscope 2 introduced into the organs. The receiving device 4 successively receives the image signals wirelessly transmitted by the capsule endoscope 2 in the subject 1, via the receiving antennas 3a to 3h and obtains the group of in-vivo images of the subject 1 captured by the capsule endoscope 2. The receiving device 4 has the portable recording medium 6 removably attached thereto and records the group of in-vivo images of the subject 1 obtained from the capsule endoscope 2 in the portable recording medium 6.

The receiving device 4 has a wireless interface for establishing a wireless communication to the viewer 7. The receiving device 4 wirelessly transmits the image signal received from the capsule endoscope 2 to the viewer 7 via the receiving antennas 3a to 3h in real time through the wireless interface. In this example, the receiving device 4 performs a receiving process and a transmission process for the image signal by temporally separating a receiving period for receiving the image signal from the capsule endoscope 2 via the receiving antennas 3a to 3h and a transmitting period for wirelessly transmitting the image signal to the viewer 7. That is, during a non-receiving period immediately after the receiving period for the image signal, the receiving device 4 wirelessly transmits the image signal from the capsule endoscope 2 received in the receiving period to the viewer 7.

The receiving period for the image signal in the receiving device 4 (hereinafter, also "receiving period of the receiving device 4") is a period in which the receiving device 4 receives the image signal from the capsule endoscope 2 via the receiving antennas 3*a* to 3*h*, and corresponds to a transmitting period in which the capsule endoscope 2 wirelessly transmits the image signal including the in-vivo image of the subject 1. The non-receiving period for the image signal in the receiving device 4 (hereinafter, also "non-receiving period of the receiving device 4") is a period in which the receiving device 4 does not receive the image signal from the capsule endoscope 2, that is, a period from when the receiving device 4 completes reception of the image signal until when the receiving device 4 receives the image signal of a next frame. The non-receiving period of the receiving device 4 corresponds to a non-transmitting period in which the capsule endoscope 2 does not wirelessly transmit the image signal.

The receiving antennas 3*a* to 3*h* are discretely arranged on a body surface of the subject 1 along a transfer path of the capsule endoscope 2 introduced into the organs of the subject 1 (that is, digestive tract of the subject 1), for example, and are connected to the receiving device 4. These receiving antennas 3*a* to 3*h* each acquire the image signals successively wirelessly transmitted from the capsule endoscope 2 within the subject 1 and successively transmit the acquired image signals to the receiving device 4. The receiving antennas 3*a* to 3*h* can be discretely arranged on a jacket or the like worn by the subject 1. What is required is that one or more receiving antennas that acquire the image signals are arranged on the subject 1, and the number of the arranged antennas is not particularly limited to eight.

The image display device 5 has a configuration like a workstation that obtains various data such as the group of in-vivo images of the subject 1 through the portable recording medium 6 and displays the obtained various data on a display. Specifically, the image display device 5 is removably attached with the portable recording medium 6 having the group of in-vivo images of the subject 1 recorded therein, and loads therein the group of in-vivo images of the subject 1 from the attached portable recording medium 6. The image display device 5 displays the in-vivo images of the subject 1 according to a predetermined operation of a user such as a doctor and a nurse. The user such as a doctor and a nurse observes the in-vivo images of the subject 1 displayed by the image display device 5, and examines insides of the organs of the subject 1 through the observation of the in-vivo images to make a diagnosis of the subject 1.

The portable recording medium 6 is a transportable recording medium and enables transfer of data between the receiving device 4 and the image display device 5. Specifically, the portable recording medium 6 has a configuration capable of being attached to or detached from the receiving device 4 or the image display device 5, and outputting or recording data during attachment to the device 4 or 5. The portable recording medium 6 records therein the group of in-vivo images of the subject 1 received by the receiving device 4 from the capsule endoscope 2 and the like when attached to the receiving device 4. The portable recording medium 6 transmits the recorded data such as the group of in-vivo images of the subject 1 to the image display device 5 when attached to the image display device 5.

The various data recorded in the portable recording medium 6 includes the group of in-vivo images of the subject 1, time information (such as an imaging time and a receiving time) of each in-vivo image of the group of in-vivo images, patient information of the subject 1, and examination information of the subject 1, for example. The patient information of the subject 1 is identification information for identifying the subject 1 and includes a patient name, a patient ID, a date of birth, a sex, and an age of the subject 1, for example. The examination information of the subject 1 is identification information for identifying a capsule endoscope examination to be performed for the subject 1 (examination for observing insides of organs performed by introducing the capsule endoscope 2 into the organs), and includes an examination ID and an examination date, for example.

The viewer 7 serves as a real-time display device that displays in real time the in-vivo images received by the receiving device 4 from the capsule endoscope 2 in the subject 1. Specifically, the viewer 7 is a transportable display device including a wireless interface for the receiving device 4 and a display function for the in-vivo images. The viewer 7 successively receives the image signals from the receiving device 4 through the wireless interface and successively displays in real time the group of in-vivo images included in the received image signals (specifically, the in-vivo images of the subject 1 captured by the capsule endoscope 2).

Figure 2:
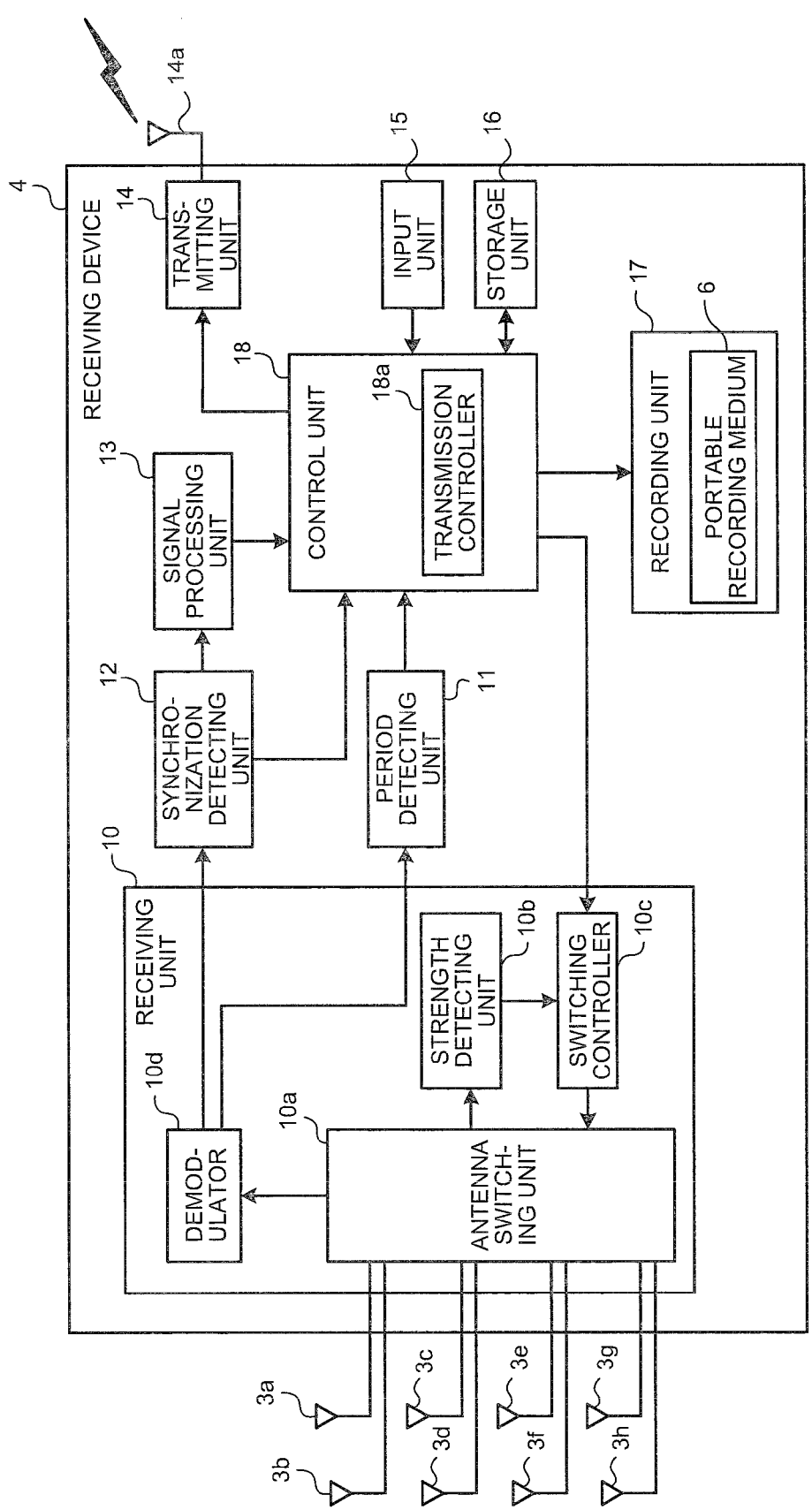
FIG. 2 is a schematic block diagram of a configuration example of a receiving device according to the first embodiment of the present invention.

A configuration of the receiving device 4 according to the first embodiment of the present invention is explained next. FIG. 2 is a schematic block diagram of a configuration example of the receiving device 4 according to the first embodiment of the present invention. As shown in FIG. 2, the receiving device 4 according to the first embodiment includes a receiving unit 10 that receives the image signal from the capsule endoscope 2 via the receiving antennas 3*a* to 3*h*, a period detecting unit 11 that detects a period in which the receiving unit 10 does not receive the image signal from the capsule endoscope 2, a synchronization detecting unit 12 that detects a synchronizing signal included in the image signal received by the receiving unit 10, a signal processing unit 13 that performs image processing of the image signal in frame unit, including the synchronizing signal detected by the synchronization detecting unit 12, and a transmitting unit 14 that wirelessly transmits the image signal received by the receiving unit 10 to the viewer 7. The receiving device 4 further includes an input unit 15, a storage unit 16, a recording unit 17 that records the group of in-vivo images of the subject 1 in the portable recording medium 6, a control unit 18 that controls these constituent units of the receiving device 4, and a power supply unit (not shown) that supplies power to the constituent units of the receiving device 4.

The receiving unit 10 receives the image signal including the in-vivo image of the subject 1, which is captured by the capsule endoscope 2, via the receiving antennas 3*a* to 3*h*. In this example, the receiving unit 10 receives a wireless signal corresponding to the image signal from the capsule endoscope 2 via the receiving antennas 3*a* to 3*h*. The receiving unit 10 includes an antenna switching unit 10*a* connected to the receiving antennas 3*a* to 3*h*, a strength detecting unit 10*b* that detects a received field strength of the wireless signal received via the receiving antennas 3*a* to 3*h*, a switching controller 10*c* that controls an antenna switching operation by the antenna switching unit 10*a*, and a demodulator 10*d* that demodulates the wireless signal received through the antenna switching unit 10*a* into a baseband signal (an image signal), as shown in FIG. 2.

The antenna switching unit 10*a* includes the receiving antennas 3*a* to 3*h* and performs an antenna switching operation to switch a connection status between each of the receiving antennas 3*a* to 3*h* and the demodulator 10*d*. More specifically, the antenna switching unit 10*a* successively switches the receiving antennas 3*a* to 3*h* to be connected to the demodulator 10*d* and successively transmits the wireless signals received via the receiving antennas 3*a* to 3*h* to the strength detecting unit 10b, under control of the switching controller 10c. The antenna switching unit 10a performs the antenna switching operation under control of the switching controller 10c to select one of the receiving antennas 3a to 3h appropriate for receiving the wireless signal from the capsule endoscope 2, and connects the selected receiving antenna (any one of the receiving antennas 3a to 3h) to the demodulator 10d.

The strength detecting unit 10b detects a received field strength of each of the wireless signals successively received via the receiving antennas 3a to 3h. Specifically, the strength detecting unit 10b detects a received field strength of each of the wireless signals successively received from the capsule endoscope 2 via the receiving antennas 3a to 3h successively switched by the antenna switching unit 10a. The strength detecting unit 10b transmits a signal such as a received signal strength indicator (RSSI) to the switching controller 10c as a result of the detection of the received field strength.

The switching controller 10c controls the antenna switching unit 10a to successively switch the connection statuses between the receiving antennas 3a to 3h and the demodulator 10d under control of the control unit 18. The switching controller 10c selects one of the receiving antennas 3a to 3h that provides a greatest received field strength of the wireless signal based on the signal indicating the received field strength (for example, the RSSI signal) detected by the strength detecting unit 10b, and controls the antenna switching unit 10a to connect the selected receiving antenna to the demodulator 10d.

The demodulator 10d demodulates the wireless signal received from the capsule endoscope 2 via the receiving antennas 3a to 3h into the image signal as the baseband signal. Specifically, the demodulator 10d performs demodulation or the like of the wireless signal received via the receiving antenna (one of the receiving antennas 3a to 3h) selected by the antenna switching unit 10a to extract the image signal from the wireless signal. The image signal extracted by the demodulator 10d is a baseband signal including at least image data (in-vivo image of the subject 1) captured by the capsule endoscope 2. The demodulator 10d transmits the image signal to the synchronization detecting unit 12. Upon receipt of the wireless signal from the capsule endoscope 2 via the receiving antennas 3a to 3h, the demodulator 10d transmits receiving start information indicating that the receiving unit 10 starts receiving the image signal from the capsule endoscope 2 corresponding to the wireless signal, to the period detecting unit 11. Upon transmission of the image signal from the capsule endoscope 2 to the synchronization detecting unit 12, the demodulator 10d transmits receiving end information indicating that the receiving unit 10 has ended receiving the image signal from the capsule endoscope 2, to the period detecting unit 11.

The period detecting unit 11 detects a period in which the receiving unit 10 does not receive the image signal from the capsule endoscope 2 (that is, a non-receiving period of the receiving device 4). Specifically, the period detecting unit 11 measures a time by using a crystal oscillator, for example, and, each time the receiving start information or the receiving end information is obtained from the demodulator 10d, successively detects a time when the information is obtained. The period detecting unit 11 successively detects a time (a receiving end time) when the receiving end information of the image signal of a (n-1)th (n is a positive integer) frame including an in-vivo image $P_{n-1}$ of the (n-1)th frame is obtained and a time (a receiving start time) when the receiving start information of the image signal of the next frame, that is, an nth frame including an in-vivo image $P_n$ of the nth frame is obtained. The period detecting unit 11 then calculates a time interval $\Delta T_n$ which is a time difference between the receiving start time and the receiving end time. The period detecting unit 11 then detects a receiving end time when receiving end information of the image signal of the nth frame is obtained. In timing of detecting the receiving end time of the image signal of the nth frame, the period detecting unit 11 transmits non-receiving period information indicating a non-receiving period (time interval $\Delta T_n$) immediately after the receiving period for the image signal of the (n-1)th frame (hereinafter, "non-receiving period information of the (n-1)th frame") to the control unit 18. The period detecting unit 11 has a default time interval $\Delta T_1$ previously set. When detecting a receiving end time when receiving end information of the image signal of a 1st frame is obtained, the period detecting unit 11 transmits the default time interval $\Delta T_1$ for estimating a non-receiving period immediately after a receiving period for the image signal of the 1st frame as the non-receiving period information, to the control unit 18 in timing when the receiving end time of the image signal of the 1st frame is detected.

The synchronization detecting unit 12 obtains the image signal extracted by the demodulator 10d and detects a synchronizing signal (vertical and horizontal synchronizing signals) included in the obtained image signal. Accordingly, the synchronization detecting unit 12 detects a head and an end of the image signal in frame unit corresponding to an in-vivo image of one frame, and transmits the image signal in frame unit to the signal processing unit 13 and the control unit 18 upon each detection thereof.

The signal processing unit 13 obtains the image signal in frame unit from the synchronization detecting unit 12, and performs predetermined image processing for the obtained image signal in frame unit upon each obtaining, to successively generate an in-vivo image in frame unit corresponding to the image signal in frame unit (specifically, in-vivo image of the subject 1 captured by the capsule endoscope 2). The signal processing unit 13 successively transmits the generated in-vivo image of the subject 1 to the control unit 18.

The transmitting unit 14 wirelessly transmits the image signal from the capsule endoscope 2, received via the receiving antennas 3a to 3h by the receiving unit 10, to the viewer 7. Specifically, the transmitting unit 14 includes a transmitting antenna 14a and serves as a wireless interface for the viewer 7. The transmitting unit 14 obtains the image signal in frame unit under the control of the control unit 18 and performs predetermined modulation of the obtained image signal in frame unit to generate a wireless signal corresponding to the image signal in frame unit. The transmitting unit 14 wirelessly transmits the wireless signal to the viewer 7 via the transmitting antenna 14a during the non-receiving period immediately after the receiving period for the image signal in frame unit.

The input unit 15 is realized using an input key, an input button, or the like, for information input and inputs to the control unit 18 various kinds of instruction information for instructing the control unit 18 according to an input operation of the user. The storage unit 16 is realized using a storage device such as a random access memory (RAM), and temporarily stores therein the image signal before being transmitted, the non-receiving period information, and the like, until the control unit 18 causes the transmitting unit 14 to wirelessly transmit the image signal from the capsule endoscope 2. The information stored in the storage unit 16 is read by the control unit 18 as necessary.

The recording unit 17 is for recording the group of in-vivo images of the subject 1 received from the capsule endoscope 2. Specifically, the recording unit 17 is removably attached with the portable recording medium 6, and records the group of in-vivo images of the subject 1 in the portable recording medium 6 under the control of the control unit 18.

The control unit 18 is realized using a central processing unit (CPU) that executes processing programs, a read only memory (ROM) that has the processing programs and the like previously stored therein, and a RAM that stores therein operation parameters and the like. The control unit 18 controls the constituent units of the receiving device 4 and controls input and output of signals between the constituent units. For example, the control unit 18 controls input of information by the input unit 15. The control unit 18 obtains the image signal from the synchronization detecting unit 12 and the non-receiving period information from the period detecting unit 11. The control unit 18 stores the image signal and the non-receiving period information associated with each other in the storage unit 16, and reads the image signal or the non-receiving period information from the storage unit 16 as necessary. The control unit 18 controls the switching controller 10c, and controls the antenna switching unit 10a through the control by the switching controller 10c. The control unit 18 controls the signal processing unit 13 to generate an in-vivo image corresponding to one frame based on the image signal in frame unit outputted by the synchronization detecting unit 12, and to output the generated in-vivo image. The control unit 18 controls the recording unit 17 to successively record the in-vivo images successively obtained from the signal processing unit 13 in the portable recording medium 6.

The control unit 18 includes a transmission controller 18a that controls the transmitting unit 14. The transmission controller 18a transmits the image signal obtained from the synchronization detecting unit 12 (more specifically, the image signal from the capsule endoscope 2) to the transmitting unit 14 and controls the transmitting unit 14 to wirelessly transmit the image signal to the external viewer 7. In this example, the transmission controller 18a estimates a non-receiving period immediately after a receiving period in which the wireless-transmission-target image signal to be wirelessly transmitted by the transmitting unit 14 is received by the receiving unit 10, based on the non-receiving period information detected by the period detecting unit 11 and timing when the non-receiving period information is obtained. The transmission controller 18a then controls the transmitting unit 14 to wirelessly transmit the wireless-transmission-target image signal during the estimated non-receiving period. In this way, the transmission controller 18a controls the transmitting unit 14 to wirelessly transmit the image signal from the capsule endoscope 2 to the viewer 7 by temporally separating a receiving period for the image signal from the capsule endoscope 2 and a transmitting period for the image signal to the viewer 7. The transmitting unit 14 transmits and receives a predetermined wave to and from a receiving unit 20 (shown in FIG. 3) of the viewer 7 to establish a connection with the receiving unit 20 before wirelessly transmitting the image signal from the capsule endoscope 2 to the viewer 7. The transmission controller 18a controls the transmitting unit 14 to perform the establishment of the connection with the receiving unit 20 also during the non-receiving period immediately after the receiving period.

Figure 3:
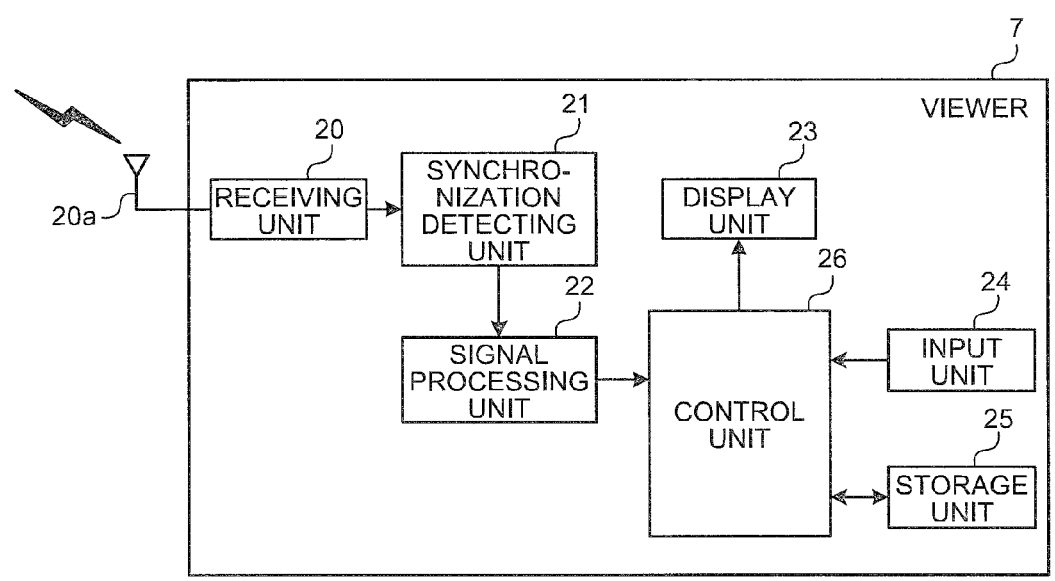
FIG. 3 is a schematic block diagram of a configuration example of a viewer that displays in-vivo images of a subject in real time.

A configuration of the viewer 7 that displays the in-vivo images of the subject 1 received by the receiving device 4 in real time is explained next. FIG. 3 is a schematic block diagram of a configuration example of the viewer 7 that displays the in-vivo images of the subject 1 in real time. As shown in FIG. 3, the viewer 7 includes the receiving unit 20 and a receiving antenna 20a that serve as a wireless interface for receiving the image signal wirelessly transmitted by the receiving device 4, a synchronization detecting unit 21 that detects the synchronizing signal which is included in the image signal received by the receiving unit 20, a signal processing unit 22 that performs image processing of the image signal in frame unit including the synchronizing signal detected by the synchronization detecting unit 21, and a display unit 23 that displays the in-vivo image included in the image signal. The viewer 7 also includes an input unit 24, a storage unit 25, a control unit 26 that controls the constituent units of the viewer 7, and a power supply unit (not shown) that supplies power to the constituent units of the viewer 7.

The receiving unit 20 includes the receiving antenna 20a for transmitting or receiving the wireless signal to/from the transmitting antenna 14a of the receiving device 4, and receives the image signal from the receiving device 4 via the receiving antenna 20a. Specifically, the receiving unit 20 receives the wireless signal transmitted by the transmitting unit 14 of the receiving device 4 via the receiving antenna 20a, and performs demodulation or the like of the received wireless signal to extract an image signal from the wireless signal. The image signal extracted by the receiving unit 20 is the image signal received from the capsule endoscope 2 by the receiving device 4, and is a baseband signal including at least the image data (in-vivo image of the subject 1) captured by the capsule endoscope 2. The receiving unit 20 transmits the image signal to the synchronization detecting unit 21.

The synchronization detecting unit 21 obtains the image signal extracted by the receiving unit 20 and detects the synchronizing signal (the vertical and horizontal synchronizing signals) included in the obtained image signal. Accordingly, the synchronization detecting unit 21 detects the head and end of the image signal in frame unit corresponding to an in-vivo image of one frame, and transmits the image signal in frame unit to the signal processing unit 22 upon each detection.

The signal processing unit 22 obtains the image signal in frame unit from the synchronization detecting unit 21. The signal processing unit 22 performs predetermined image processing of the obtained image signal in frame unit upon each obtaining to successively generate the in-vivo image in frame unit corresponding to the image signal in frame unit (more specifically, the in-vivo image of the subject 1 captured by the capsule endoscope 2). The signal processing unit 22 successively transmits the generated in-vivo image of the subject 1 to the control unit 26.

The display unit 23 is realized using a display device such as a liquid crystal display, and successively displays in real time the in-vivo image successively received by the receiving unit 20 from the receiving device 4 (specifically, the in-vivo image of the subject 1 captured by the capsule endoscope 2). In this example, the display unit 23 successively displays the in-vivo image successively generated and outputted by the signal processing unit 22 according to time series under control of the control unit 26.

The input unit 24 is realized using an input key, an input button, or the like, for information input and inputs various kinds of instruction information to the control unit 26 to instruct the control unit 26 according to an input operation of the user. The storage unit 25 is realized using a storage device such as a RAM, and temporarily stores therein in-vivo images before being displayed until the control unit 26 causes the display unit 23 to display the in-vivo images. The in-vivo images stored in the storage unit 25 are read by the control unit 26 as necessary.

The control unit 26 is realized using a CPU that executes processing programs, a ROM that has the processing programs and the like previously stored therein, and a RAM that stores therein operation parameters and the like. The control unit 26 controls the constituent units of the viewer 7 and controls input and output of signals between the constituent units. For example, the control unit 26 controls information input by the input unit 24, and controls start or end of reception of the image signal by the receiving unit 20 based on the instruction information inputted by the input unit 24. The control unit 26 controls the signal processing unit 22 to generate an in-vivo image corresponding to one frame based on the image signal in frame unit outputted by the synchronization detecting unit 21, and output the generated in-vivo image. The control unit 26 controls the display unit 23 to successively display the in-vivo images successively obtained from the signal processing unit 22 according to time series. In this example, the control unit 26 temporarily stores the in-vivo images successively obtained from the signal processing unit 22 in the storage unit 25, and causes the display unit 23 to display the in-vivo images successively read from the storage unit 25 according to time series. Accordingly, the control unit 26 causes the display unit 23 to successively display in real time the in-vivo images of the subject 1, received by the receiving device 4 from the capsule endoscope 2 within the subject 1.

Figure 4:
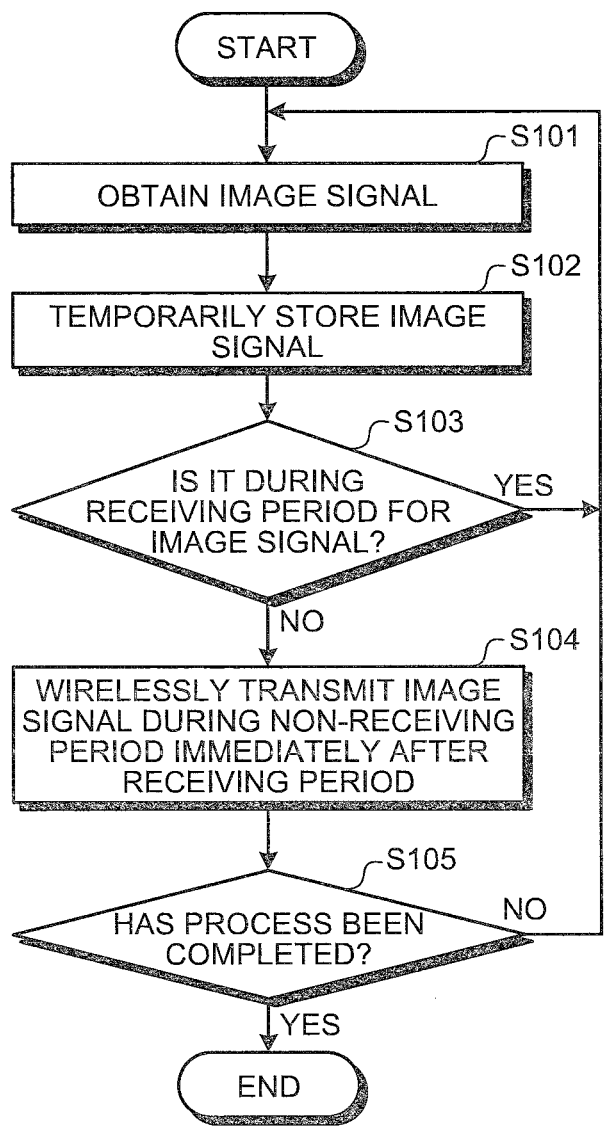
FIG. 4 is a flowchart of an example of a process procedure performed by a control unit of the receiving device according to the first embodiment.

An operation of the receiving device 4 according to the first embodiment of the present invention is explained next. FIG. 4 is a flowchart of an example of a process procedure performed by the control unit 18 of the receiving device 4 according to the first embodiment. The receiving device 4 receives the image signal wirelessly transmitted by the capsule endoscope 2, as described above. The control unit 18 temporally separates a receiving period for the image signal from the capsule endoscope 2 and a transmitting period for the image signal to the viewer 7, and controls the transmitting unit 14 to successively wirelessly transmit the image signals successively received from the capsule endoscope 2 to the viewer 7 according to the time series.

That is, as shown in FIG. 4, the control unit 18 obtains the image signal received from the capsule endoscope 2 within the subject 1 via the receiving antennas 3a to 3h (Step S101), and temporarily stores the obtained image signal in the storage unit 16 (Step S102). The control unit 18 then determines whether it is currently a receiving period for the image signal (Step S103).

At Step S103, when a receiving end signal for the image signal of an nth frame (for example, non-receiving period information of an (n-1)th frame) is not obtained from the period detecting unit 11, the control unit 18 determines it is currently a receiving period for the image signal of the nth frame (YES at Step S103). The control unit 18 then returns to Step S101 and repeats the process procedure from Step S101. When the receiving end signal for the image signal of the nth frame is obtained from the period detecting unit 11, the control unit 18 determines it is not during the receiving period for the image signal of the nth frame (it is during a non-receiving period). In this case, the control unit 18 has completely obtained the image signal in frame unit including the in-vivo image of the nth frame via the synchronization detecting unit 12, and temporarily stored the image signal in frame unit in the storage unit 16 at Step S102. The control unit 18 stores the image signal of the nth frame and the non-receiving period information of the (n-1)th frame associated with each other in the storage unit 16, and holds and manages the image signal of the nth frame and the non-receiving period information of the (n-1)th frame to be read as necessary.

When it is determined at Step S103 that it is currently not the receiving period for the image signal of the nth frame (NO at Step S103), the control unit 18 performs a control to wirelessly transmit the image signal during this non-receiving period immediately after the receiving period (Step S104). At Step S104, the transmission controller 18a estimates the non-receiving period immediately after the receiving period for the image signal of the nth frame based on the time interval $\Delta T_n$ (time interval from when reception of the image signal of the (n-1)th frame is ended until when reception of the image signal of the nth frame is started), which is non-receiving period information of the (n-1)th frame obtained at a receiving end time for the image signal of the nth frame, and timing when the non-receiving period information is obtained. The transmission controller 18a reads the image signal of the nth frame from the storage unit 16, and transmits the read image signal of the nth frame to the transmitting unit 14 as well as controlling the transmitting unit 14 to wirelessly transmit the image signal of the nth frame during the estimated non-receiving period. The image signal of the nth frame wirelessly transmitted by the transmitting unit 14 during the estimated non-receiving period is received by the viewer 7. A basis of the calculation of the non-receiving period for the nth frame is only required to be a non-receiving period for a frame prior to the nth frame and is not limited to the time interval $\Delta T_{n-1}$ of the non-receiving period of the (n-1)th frame.

Thereafter, the control unit 18 determines whether to complete the process (Step S105). When the process is not completed (NO at Step S105), the control unit 18 returns to Step S101 and repeats the process procedure from Step S101. When the input unit 15 inputs instruction information indicating process completion for example, the control unit 18 determines to complete the process (YES at Step S105) and ends the process.

Figure 5:
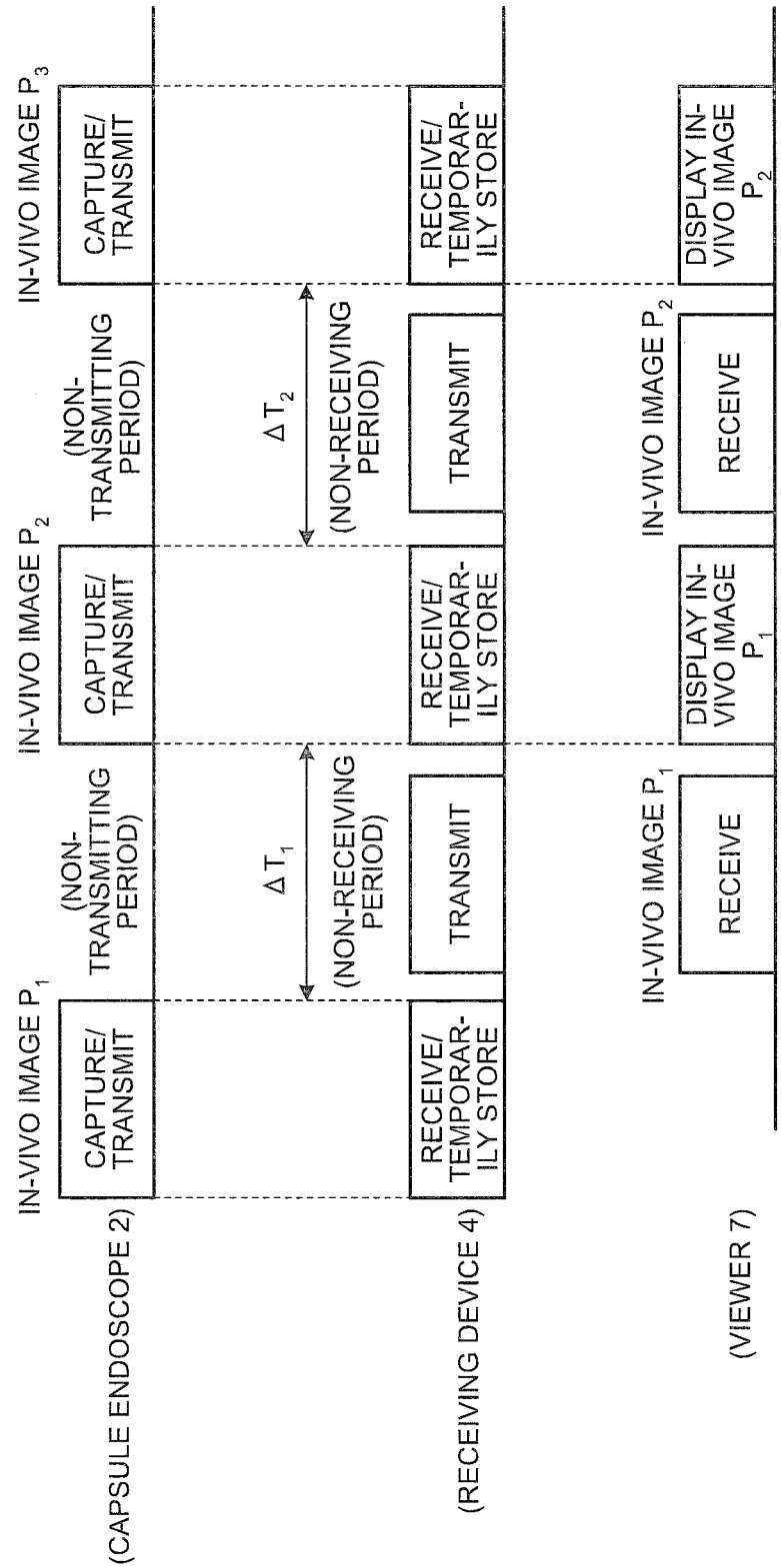
FIG. 5 is a schematic diagram of an example of a sequential control in a receiving device that wirelessly transmits an image signal to the viewer during a non-receiving period of the receiving device.

An operation of the transmission controller 18a that performs the control to wireless transmit the image signal from the capsule endoscope 2 to the viewer 7 during the non-receiving period for the image signal is specifically explained next, using the image signals of 1st to 3rd frames received from the capsule endoscope 2 within the subject 1 as an example. FIG. 5 is a schematic diagram of an example of a sequential control in the receiving device 4 that wirelessly transmits the image signal to the viewer 7 during the non-receiving period of the receiving device 4.

As shown in FIG. 5, when the capsule endoscope 2 within the subject 1 captures an in-vivo image $P_1$ of the 1st frame and wirelessly transmits the image signal of the 1st frame including the in-vivo image $P_1$, the receiving device 4 receives the image signal of the 1st frame from the capsule endoscope 2 and temporarily stores therein the received image signal of the 1st frame. The receiving device 4 wirelessly transmits the image signal of the 1st frame to the viewer 7 during a non-receiving period immediately after a receiving period for the image signal of the 1st frame.

In the receiving device 4, the transmission controller 18a estimates the non-receiving period immediately after the receiving period for the image signal of the 1st frame based on the default time interval $\Delta T_1$ and a receiving end time for the image signal of the 1st frame, which are transmitted from the period detecting unit 11. The transmission controller 18a transmits the image signal of the 1st frame temporarily stored in the storage unit 16 to the transmitting unit 14, and controls the transmitting unit 14 to wirelessly transmit the image signal of the 1st frame during the estimated non-receiving period (within the default time interval $\Delta T_1$).

The non-receiving period immediately after the receiving period for the image signal of the 1st frame corresponds to a period from when the capsule endoscope 2 ends transmitting the image signal (in-vivo image $P_1$) of the 1st frame until when the capsule endoscope 2 starts transmitting the image signal (in-vivo image $P_2$) of the 2nd frame, that is, a non-transmitting period immediately after a transmitting period for the in-vivo image $P_1$ of the 1st frame, as shown in FIG. 5.

The image signal of the 1st frame wirelessly transmitted by the receiving device 4 during the non-receiving period is received by the viewer 7. The viewer 7 generates the in-vivo image $P_1$ of the subject 1 based on the image signal of the 1st frame received from the receiving device 4, and displays the generated in-vivo image $P_1$ in real time.

When the capsule endoscope 2 captures the in-vivo image $P_2$ of the 2nd frame and wirelessly transmits the image signal of the 2nd frame including the in-vivo image $P_2$, the receiving device 4 receives the image signal of the 2nd frame from the capsule endoscope 2 and temporarily stores therein the received image signal of the 2nd frame. The receiving device 4 wirelessly transmits the image signal of the 2nd frame to the viewer 7 during a non-receiving period immediately after a receiving period for the image signal of the 2nd frame.

In the receiving device 4, the transmission controller 18*a* estimates the non-receiving period immediately after the receiving period for the image signal of the 2nd frame based on a time interval $\Delta T_2$ and a receiving end time for the image signal of the 2nd frame, which are detected by the period detecting unit 11. The time interval $\Delta T_2$ is calculated by the period detecting unit 11 as a time difference between the receiving end time for the image signal of the 1st frame and a receiving start time for the image signal of the 2nd frame (actual measured value). The transmission controller 18*a* transmits the image signal of the 2nd frame temporarily stored in the storage unit 16 to the transmitting unit 14, and controls the transmitting unit 14 to wirelessly transmit the image signal of the 2nd frame during the estimated non-receiving period (within the time interval $\Delta T_2$).

The non-receiving period immediately after the receiving period for the image signal of the 2nd frame corresponds to a period from when the capsule endoscope 2 ends transmitting the image signal (in-vivo image $P_2$) of the 2nd frame until when the capsule endoscope 2 starts transmitting the image signal (in-vivo image $P_3$) of the 3rd frame, that is, a non-transmitting period immediately after a transmitting period for the in-vivo image $P_2$ of the 2nd frame, as shown in FIG. 5.

The image signal of the 2nd frame wirelessly transmitted by the receiving device 4 during the non-receiving period is received by the viewer 7, like the image signal of the 1st frame. The viewer 7 generates the in-vivo image $P_2$ of the subject 1 based on the image signal of the 2nd frame received from the receiving device 4, and displays the generated in-vivo image $P_2$ in real time.

With respect to the image signals of the 3rd and subsequent frames successively received from the capsule endoscope 2, the receiving device 4 including the transmission controller 18*a* successively wirelessly transmits the image signals of the 3rd and subsequent frames to the viewer 7 during a non-receiving period immediately after a receiving period for each image signal, like the image signal of the 2nd frame. In the receiving device 4, the period detecting unit 11 successively detects non-receiving period information of (n-1)th frame including the time interval $\Delta T_n$ between the receiving end time for the image signal of the (n-1)th frame and the receiving start time for the image signal of the nth frame, and successively transmits the non-receiving period information of the (n-1)th frame to the control unit 18 in timing when the receiving end time for the image signal of the nth frame is detected. The transmission controller 18*a* successively estimates the non-receiving period immediately after the receiving period for the image signal of the nth frame based on the non-receiving period information of the (n-1)th frame and obtaining timing for the non-receiving period information of the (n-1)th frame, and controls the transmitting unit 14 to successively wirelessly transmit the image signals of the 3rd and subsequent frames during the non-receiving period immediately after the receiving period for each image signal, like the image signal of the 2nd frame.

The viewer 7 successively generates in-vivo images $P_3, \ldots, P_n$ of the 3rd and subsequent frames received from the receiving device 4 and successively displays the generated in-vivo images $P_3, \ldots, P_n$ in real time, like the image signal of the 2nd frame.

As described above, according to the first embodiment of the present invention, the image signal wirelessly transmitted by the in-vivo-image acquiring device such as the capsule endoscope (that is, the image signal including the in-vivo image of the subject captured by the in-vivo-image acquiring device) is received via the receiving antenna, the non-receiving period immediately after the receiving period in which the image signal is received is detected, and the image signal is wirelessly transmitted to outside during the detected non-receiving period. Accordingly, the transmitting period for the in-vivo-image acquiring device to wirelessly transmit the image signal, that is, the receiving period for the image signal to be received from the in-vivo-image acquiring device, and the transmitting period for the received image signal to be wirelessly transmitted to outside can be temporally separated. As a result, the receiving device that can wirelessly transmit in real time the image signal from the in-vivo-image acquiring device received via the receiving antenna to the external display device (more specifically, the real-time display device that displays in real time the in-vivo image of the subject included in the image signal), and also can prevent interference between the image signal wirelessly transmitted and the image signal received via the receiving antenna can be realized.

Because the receiving period for the image signal from the in-vivo-image acquiring device and the transmitting period for the image signal to the external display device are temporally separated, power consumption can be reduced as compared to a case where an image signal is received via a receiving antenna while an image signal in a different frequency band is wirelessly transmitted to an external display device during the same time period. This facilitates power saving of the receiving device. There is no need to provide an electromagnetic shield within the casing, which is required when the image signals in different frequency bands are transmitted or received during the same time period. Accordingly, downsizing of the receiving device can be facilitated, and operability and portability of the receiving device can be enhanced.

Further, the control is also performed to establish the connection between the transmitting unit that wirelessly transmits the image signal from the in-vivo-image acquiring device to the external display device, and the receiving unit of the external display device during the non-receiving period immediately after the receiving period of the receiving device. Therefore, interference between the image signal received from the in-vivo-image acquiring device via the receiving antenna and other wireless signals can be reliably avoided.

When the receiving device according to the first embodiment of the present invention is applied, the in-vivo image captured by the in-vivo-image acquiring device within the subject can be wirelessly transmitted in real time to the external display device. Consequently, the in-vivo image received from the in-vivo-image acquiring device by the receiving device can be displayed in real time on the external display device, and usability of the external display device (that is, the real-time display device that displays the in-vivo image in real time) can be enhanced.

Second Embodiment

A second embodiment of the present invention is explained next. In the first embodiment described above, the image signal in an original data amount is wirelessly transmitted to the viewer 7 during the non-receiving period of the receiving device 4. In the second embodiment, the data amount of the image signal is reduced depending on the non-receiving period detected by the period detecting unit 11, and the reduced image signal is wirelessly transmitted to the viewer 7 during the non-receiving period.

Figure 6:
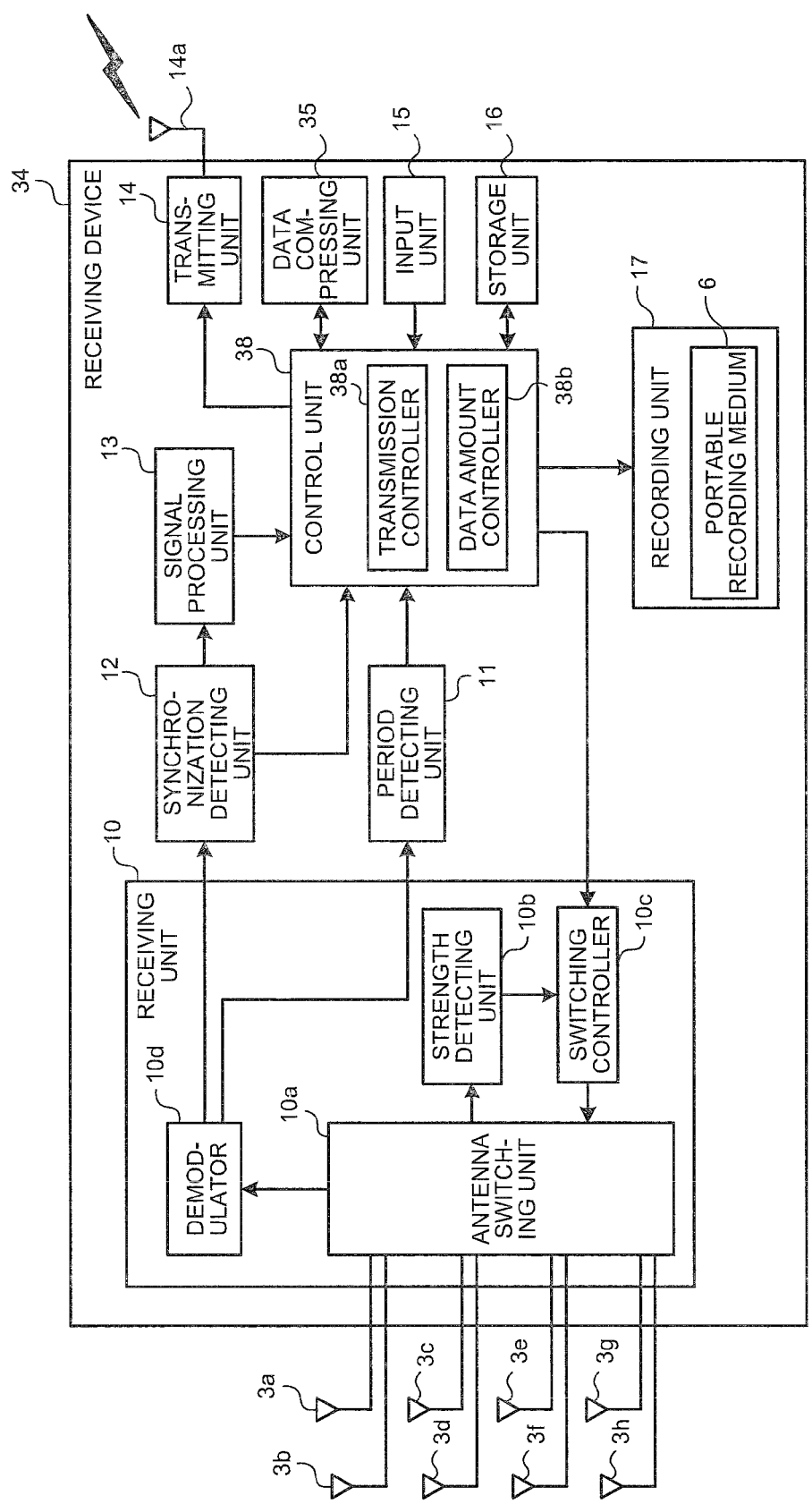
FIG. 6 is a schematic block diagram of a configuration example of a receiving device according to a second embodiment of the present invention.

FIG. 6 is a schematic block diagram of a configuration example of a receiving device according to the second embodiment of the present invention. As shown in FIG. 6, a receiving device 34 according to the second embodiment includes a control unit 38 instead of the control unit 18 of the receiving device 4 according to the first embodiment, and further includes a data compressing unit 35 that compresses an image signal to be wirelessly transmitted. Configurations other than these units are the same as those in the first embodiment, and the same constituent elements as those in the first embodiment are denoted by the same reference numerals. An in-vivo-image acquiring system according to the second embodiment of the present invention includes the receiving device 34 instead of the receiving device 4 of the in-vivo-image acquiring system according to the first embodiment (see FIG. 1).

The data compressing unit 35 serves as a data reducing unit that reduces a data amount of a wireless-transmission-target image signal to be wirelessly transmitted by the transmitting unit 14 to the external viewer 7 by compressing the data amount of the wireless-transmission-target image signal.

The control unit 38 is realized by a CPU that executes processing programs, a ROM that has the processing programs and the like previously stored therein, and a RAM that stores therein operation parameters and the like. The control unit 38 controls the constituent units of the receiving device 34 and controls input and output of signals between the constituent units. In this example, the control unit 38 controls the receiving unit 10, the period detecting unit 11, the synchronization detecting unit 12, the signal processing unit 13, the input unit 15, the storage unit 16, and the recording unit 17, like the control unit 18 of the receiving device 4 according to the first embodiment described above. The control unit 38 obtains the non-receiving period information detected by the period detecting unit 11, the image signal in frame unit outputted by the synchronization detecting unit 12, and the in-vivo image generated and outputted by the signal processing unit 13.

The control unit 38 includes a transmission controller 38a instead of the transmission controller 18a of the receiving device 4 according to the first embodiment described above, and further includes a data amount controller 38b that controls a data amount of the wireless-transmission-target image signal to be wirelessly transmitted by the transmitting unit 14. The transmission controller 38a has a similar function to that of the transmission controller 18a according to the first embodiment described above, and further has a transmission control function to wirelessly transmit the image signal compressed (reduced) by the data compressing unit 35 to the transmitting unit 14 during a non-receiving period immediately after a receiving period of the receiving device 34 or during a plurality of non-receiving periods by segmenting the signal.

The data amount controller 38b controls a data amount of the wireless-transmission-target image signal by controlling the data compressing unit 35. Specifically, the data amount controller 38b calculates a maximum amount of data that can be wirelessly transmitted during the non-receiving period immediately after the receiving period of the receiving device 34 (hereinafter, "acceptable data amount"). The data amount controller 38b determines a compression rate for the image signal based on the calculated acceptable data amount, and controls the data compressing unit 35 to compress the wireless-transmission-target image signal according to the determined compression rate. The data amount controller 38b controls the data compressing unit 35 to compress (reduce) the wireless-transmission-target image signal into an amount equal to or smaller than the acceptable data amount.

The data amount controller 38b also determines whether the in-vivo image included in the image signal compressed by the data compressing unit 35 into the amount equal to or smaller than the acceptable data amount is effective. The effective in-vivo image here has an adequate image quality to be observed by a user such as a doctor or a nurse when the image is displayed by the image display device 5 or the viewer 7. An ineffective (that is, invalid) in-vivo image means an unobservable image. The data amount controller 38b has a limit data amount previously set, which is a minimum data amount of an image signal that can include (keep) the effective in-vivo image, and compares the limit data amount and the acceptable data amount with each other. When the acceptable data amount is equal to or larger than the limit data amount as a result of the comparison, the data amount controller 38b determines that the in-vivo image included in the image signal compressed into the amount equal to or smaller than the acceptable data amount (hereinafter, also "in-vivo image in the amount equal to or smaller than the acceptable data amount") is effective. The data amount controller 38b then controls the data compressing unit 35 to compress the image signal into an amount equal to or smaller than the acceptable data amount and equal to or larger than the limit data amount. When the acceptable data amount is smaller than the limit data amount, the data amount controller 38b determines that the in-vivo image in the amount equal to or smaller than the acceptable data amount is invalid. In this case, the data amount controller 38b controls the data compressing unit 35 to compress the image signal into the limit data amount.

Figure 7:
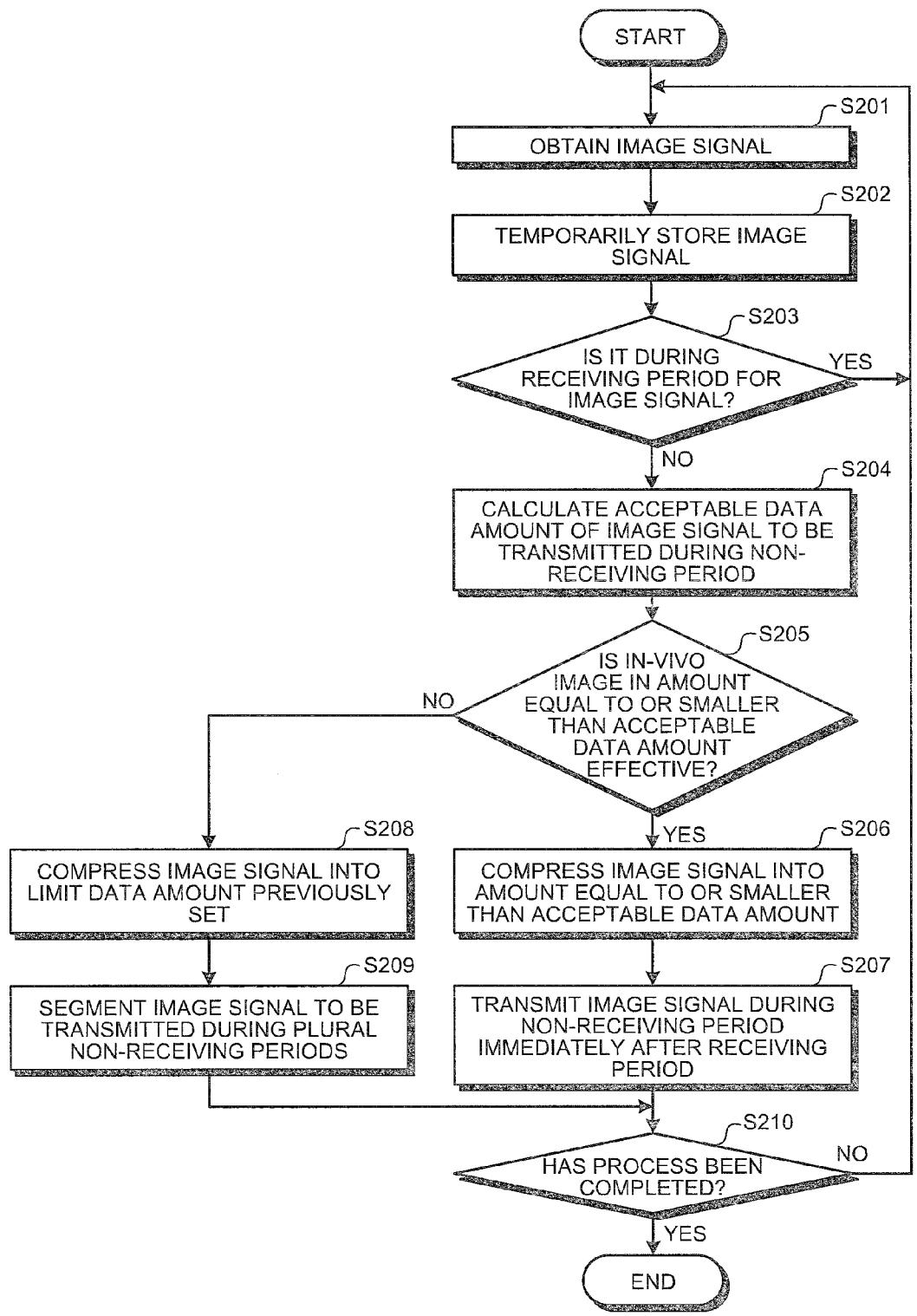
FIG. 7 is a flowchart of an example of a process procedure performed by a control unit of the receiving device according to the second embodiment of the present invention.

An operation of the receiving device 34 according to the second embodiment of the present invention is explained next. FIG. 7 is a flowchart of an example of a process procedure performed by the control unit 38 of the receiving device 34 according to the second embodiment. The receiving device 34 receives the image signal wirelessly transmitted by the capsule endoscope 2, like in the first embodiment described above. The control unit 38 temporally separates the receiving period for the image signal from the capsule endoscope 2 and the transmitting period for the image signal to the viewer 7. The control unit 38 also compresses the image signal from the capsule endoscope 2 depending on the non-receiving period immediately after the receiving period, and controls the transmitting unit 14 to successively wirelessly transmit the successively-compressed image signals to the viewer 7 according to time series.

That is, as shown in FIG. 7, the control unit 38 obtains the image signal from the capsule endoscope 2 within the subject 1 (Step S201) and temporarily stores the obtained image signal in the storage unit 16 (Step S202), like at Steps S101 and S102. The control unit 38 then determines whether it is currently a receiving period for the image signal (Step S203), like at Step S103. When it is during the receiving period for the image signal (YES at Step S203), the control unit 38 returns to Step S201 and repeats the process procedure from Step S201. The control unit 38 repeatedly performs the processes at Steps S201 to S203 until when the receiving period for the image signal ends, thereby to complete obtaining of the image signal in frame unit from the synchronization detecting unit 12, and temporarily stores the image signal in frame unit in the storage unit 16. The control unit 38 stores the obtained image signal of an nth frame and non-receiving period information of an (n-1)th frame, associated with each other, in the storage unit 16, and holds and manages the image signal of the nth frame and the non-receiving period information of the (n-1)th frame to be read as necessary.

Meanwhile, when it is determined at Step S203 that it is not currently the receiving period for the image signal (NO at Step S203), the control unit 38 calculates an acceptable data amount of the image signal to be wirelessly transmitted during this non-receiving period immediately after the receiving period (Step S204). At Step S204, based on the non-receiving period information (time interval $\Delta T_n$) of the (n-1)th frame obtained from the period detecting unit 11 and obtaining timing for the non-receiving period information of the (n-1)th frame, the data amount controller 38b estimates a non-receiving period immediately after the receiving period for the image signal of the nth frame. The data amount controller 38b then calculates the acceptable data amount of the image signal that can be wirelessly transmitted by the transmitting unit 14 within the time interval $\Delta T_n$, which is the length of the estimated non-receiving period, that is, during the non-receiving period immediately after the receiving period for the image signal of the nth frame.

The control unit 38 then determines whether the in-vivo image in an amount equal to or smaller than the acceptable data amount calculated at Step S204 is effective (Step S205). At Step S205, the data amount controller 38b compares the limit data amount and the acceptable data amount calculated at Step S204 with each other. When the acceptable data amount is equal to or larger than the limit data amount as a result of the comparison, the data amount controller 38b determines the in-vivo image in the amount equal to or smaller than the acceptable data amount is effective. When the acceptable data amount is smaller than the limit data amount, the data amount controller 38b determines the in-vivo image in the amount equal to or smaller than the acceptable data amount is ineffective (invalid).

When it is determined at Step S205 that the in-vivo image in the amount equal to or smaller than the acceptable data amount is effective (YES at Step S205), the control unit 38 controls the data compressing unit 35 to compress the image signal into the amount equal to or smaller than the acceptable data amount (Step S206). At Step S206, the data amount controller 38b determines a compression rate that enables to compress the image signal into a data amount in a range equal to or smaller than the acceptable data amount and equal to or larger than the limit data amount, and causes the data compressing unit 35 to compress the wireless-transmission-target image signal with the determined compression rate. Accordingly, the data amount controller 38b can compress the wireless-transmission-target image signal into the amount equal to or smaller than the acceptable data amount and equal to or larger than the limit data amount. When the acceptable data amount is equal to or larger than the limit data amount, the data amount controller 38b can determine a compression rate that enables to compress the image signal into the acceptable data amount equal to or larger than the limit data amount, and cause the data compressing unit 35 to compress the wireless-transmission-target image signal with the determined compression rate.

When the original data amount of the image signal from the capsule endoscope 2, obtained at Step S201, is equal to or smaller than the acceptable data amount, the data amount controller 38b does not cause the data compressing unit 35 to reduce the image signal.

The control unit 38 then obtains the wireless-transmission-target image signal compressed at Step S206, from the data compressing unit 35, and performs a control to wirelessly transmit the obtained compressed image signal during the non-receiving period immediately after the receiving period, like at Step S104 (Step S207). At Step S207, based on the non-receiving period information of the (n-1)th frame and the obtaining timing for the non-receiving period information, the transmission controller 38a estimates the non-receiving period immediately after the receiving period for the image signal of the nth frame, and controls the transmitting unit 14 to wirelessly transmit the compressed image signal of the nth frame during the estimated non-receiving period, like at Step S104. As a result, the compressed image signal of the nth frame is received by the viewer 7 during the non-receiving period.

Meanwhile, when it is determined at Step S205 that the in-vivo image in the amount equal to or smaller than the acceptable data amount is ineffective (NO at Step S205), the control unit 38 controls the data compressing unit 35 to compress the image signal into the limit data amount previously set (Step S208). At Step S208, the data amount controller 38b determines based on the limit data amount instead of the acceptable data amount, a compression rate that enables to compress the wireless-transmission-target image signal into the limit data amount, and causes the data compressing unit 35 to compress the image signal with the determined compression rate. Accordingly, the data amount controller 38b can compress the wireless-transmission-target image signal into the limit data amount.

The control unit 38 then obtains the wireless-transmission-target image signal compressed at Step S208, from the data compressing unit 35, and performs a control to segment the compressed image signal to be wirelessly transmitted during a plurality of non-receiving periods after the receiving period (Step S209). At Step S209, the transmission controller 38a estimates the non-receiving period immediately after the receiving period for the image signal of the nth frame like at Step S207, and controls the transmitting unit 14 to wirelessly transmit a part of the compressed image signal of the nth frame during the estimated non-receiving period. The transmission controller 38a then estimates based on the non-receiving period information obtained from the period detecting unit 11 and the obtaining timing for the non-receiving period information, a non-receiving period subsequent to the non-receiving period and controls the transmitting unit 14 to wirelessly transmit a part (or a remaining part) of the compressed image signal of the nth frame during the estimated subsequent non-receiving period. Until the compressed image signal of the nth frame is completely wirelessly transmitted, the transmission controller 38a repeatedly performs the control to segment the image signal and wirelessly transmit the segmented image signals during the plural non-receiving periods.

When causing the transmitting unit 14 to segment the image signal to be wirelessly transmitted during the plural non-receiving periods, the transmission controller 38a can cause the transmitting unit 14 not to wirelessly transmit successive image signals, which are originally to be wirelessly transmitted during these plural non-receiving periods, respectively.

When the process at Step S207 or S209 ends, the control unit 38 determines whether to complete the process, like at Step S105 (Step S210). When the process is not completed (NO at Step S210), the control unit 38 returns to Step S201 and repeats the process procedure from Step S201. When it is determined that the process has been completed (YES at Step S210), the control unit 38 ends the process.

Figure 8:
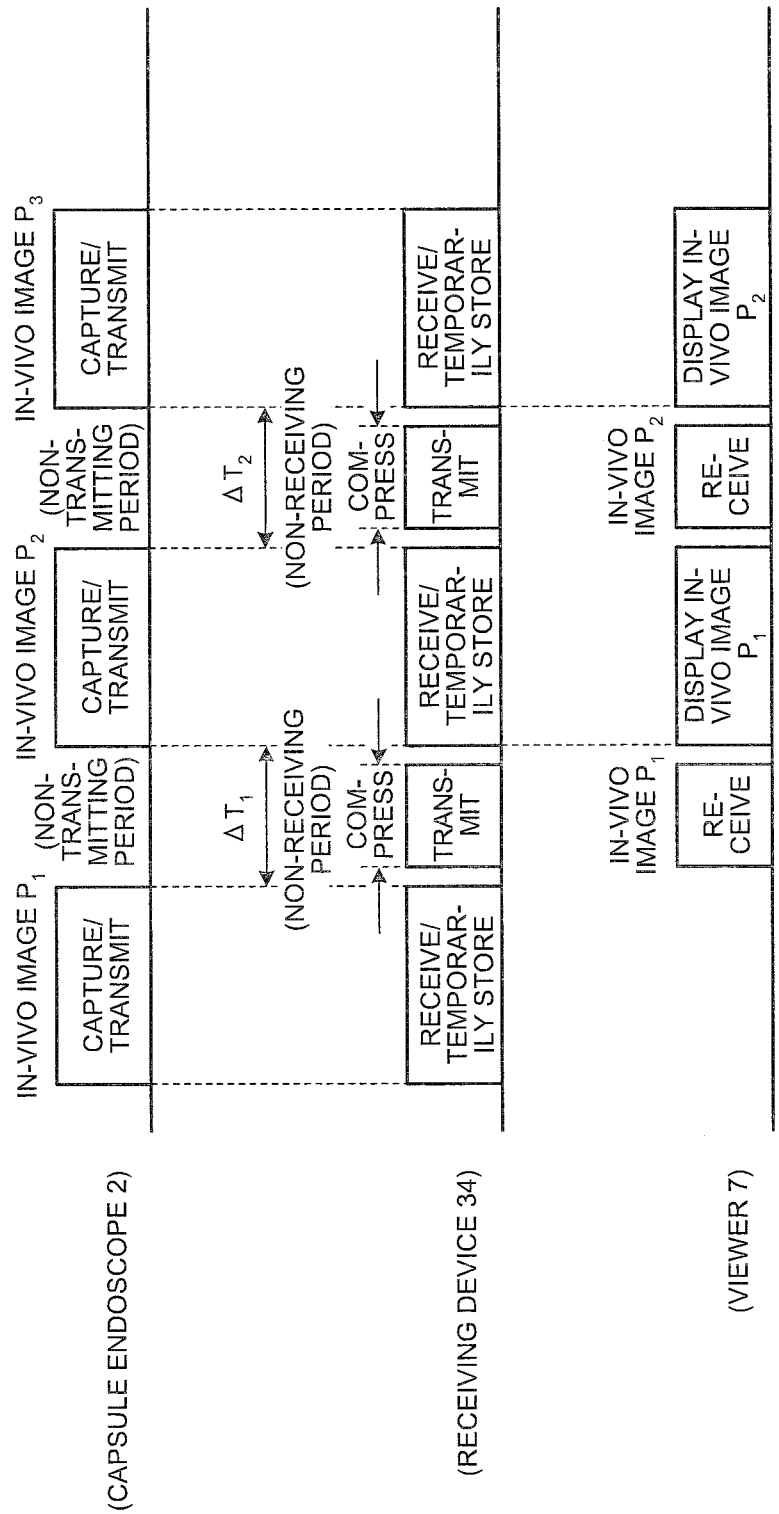
FIG. 8 is a schematic diagram of an example of a sequential control in a receiving device that wirelessly transmits a compressed image signal to a viewer during a non-receiving period of the receiving device.

An operation of the control unit 38 that performs the control to compress the image signal from the capsule endoscope 2 depending on to the non-receiving period and wirelessly transmit the compressed image signal to the viewer 7 during the non-receiving period is specifically explained next, using the image signals of 1st to 3rd frames received from the capsule endoscope 2 within the subject 1 as an example. FIG. 8 is a schematic diagram of an example of a sequential control in the receiving device 34 that wirelessly transmits the compressed image signal to the viewer 7 during the non-receiving period of the receiving device 34.

As shown in FIG. 8, when the capsule endoscope 2 within the subject 1 captures the in-vivo image $P_1$ of the 1st frame and wirelessly transmits the image signal of the 1st frame including the in-vivo image $P_1$, the receiving device 34 receives the image signal of the 1st frame from the capsule endoscope 2 and temporarily stores therein the received image signal of the 1st frame. The receiving device 34 compresses the image signal of the 1st frame depending on the non-receiving period immediately after the receiving period for the image signal of the 1st frame (that is, the default time interval $\Delta T_1$), and wirelessly transmits the compressed image signal of the 1st frame to the viewer 7 during the non-receiving period.

In the receiving device 34, the data amount controller 38b estimates based on the default time interval $\Delta T_1$ obtained from the period detecting unit 11 and the obtaining timing for the default time interval $\Delta T_1$, the non-receiving period immediately after the receiving period for the image signal of the 1st frame. The data amount controller 38b then calculates an acceptable data amount that can be wirelessly transmitted within the default time interval $\Delta T_1$, which is the length of the estimated non-receiving period, that is, during the non-receiving period immediately after the receiving period for the image signal of the 1st frame (acceptable data amount for the 1st frame). The data amount controller 38b then compares the acceptable data amount for the 1st frame and the limit data amount with each other, and determines whether the in-vivo image $P_1$ in an amount equal to or smaller than the acceptable data amount for the 1st frame is effective based on a result of the comparison.

When the acceptable data amount for the 1st frame is equal to or larger than the limit data amount, the data amount controller 38b determines the in-vivo image $P_1$ in the amount equal to or smaller than the acceptable data amount for the 1st frame is effective. The data amount controller 38b then controls the data compressing unit 35 to compress the image signal of the 1st frame (that is, the in-vivo image $P_1$) into an amount equal to or smaller than the acceptable data amount for the 1st frame and equal to or larger than the limit data amount. As a result, the transmission controller 38a obtains the compressed image signal of the 1st frame including the compressed in-vivo image $P_1$.

Like in the first embodiment described above, the transmission controller 38a estimates the non-receiving period immediately after the receiving period for the image signal of the 1st frame based on the default time interval $\Delta T_1$ and the obtaining timing for the default time interval $\Delta T_1$, and transmits the compressed image signal of the 1st frame to the transmitting unit 14. The transmission controller 38a further controls the transmitting unit 14 to wirelessly transmit the compressed image signal of the 1st frame during the estimated receiving period (within the default time interval $\Delta T_1$).

The non-receiving period immediately after the receiving period for the image signal of the 1st frame corresponds to a non-transmitting period from when the capsule endoscope 2 ends transmitting the image signal (in-vivo image $P_1$) of the 1st frame until when the capsule endoscope 2 starts transmitting the image signal (in-vivo image $P_2$) of the 2nd frame, as shown in FIG. 8. Therefore, when a frame rate of the image signals successively wirelessly transmitted by the capsule endoscope 2 is increased, the non-receiving period immediately after the receiving period for the image signal of the 1st frame is shortened accordingly. The data amount controller 38b causes the data compressing unit 35 to compress (reduce) the data amount of the image signal of the 1st frame into a data amount that can be wirelessly transmitted by the transmitting unit 14 during the non-receiving period of the receiving device 34, which is shortened with the increase in the frame rate. As a result, the transmission controller 38a can cause the transmitting unit 14 to wirelessly transmit the image signal of the 1st frame compressed by the data compressing unit 35 during the shortened non-receiving period of the receiving device 34 (that is, the non-receiving period immediately after the receiving period for the image signal of the 1st frame).

The compressed image signal of the 1st frame wirelessly transmitted by the receiving device 34 during the non-receiving period is received by the viewer 7, like in the first embodiment described above. The signal processing unit 22 of the viewer 7 performs predetermined expansion (decompression), image processing, and the like of the compressed image signal of the 1st frame to generate the in-vivo image $P_1$ of the subject 1, and displays the generated in-vivo image $P_1$ in real time.

Meanwhile, when the capsule endoscope 2 captures the in-vivo image $P_2$ of the 2nd frame and wirelessly transmits the image signal of the 2nd frame including the in-vivo image $P_2$, the receiving device 34 receives the image signal of the 2nd frame from the capsule endoscope 2 and temporarily stores therein the received image signal of the 2nd frame. The receiving device 34 compresses the image signal of the 2nd frame depending on the non-receiving period immediately after the receiving period for the image signal of the 2nd frame, and wirelessly transmits the compressed image signal of the 2nd frame to the viewer 7 during the non-receiving period.

In the receiving device 34, the data amount controller 38b estimates the non-receiving period immediately after the receiving period for the image signal of the 2nd frame based on the non-receiving period information of the 1st frame detected by the period detecting unit 11. The data amount controller 38*b* then calculates an acceptable data amount that can be wirelessly transmitted with the time interval $\Delta T_2$, which is the length of the estimated non-receiving period, that is, during the non-receiving period immediately after the receiving period for the image signal of the 2nd frame (acceptable data amount for the 2nd frame). The data amount controller 38*b* then compares the acceptable data amount for the 2nd frame and the limit data amount with each other, and determines based on a result of the comparison whether the in-vivo image $P_2$ in an amount equal to or smaller than the acceptable data amount for the 2nd frame is effective.

When the acceptable data amount for the 2nd frame is equal to or larger than the limit data amount, the data amount controller 38*b* determines the in-vivo image $P_2$ in the amount equal to or smaller than the acceptable data amount for the 2nd frame is effective. The data amount controller 38*b* then controls the data compressing unit 35 to compress the image signal of the 2nd frame (that is, the in-vivo image $P_2$) into an amount equal to or smaller than the acceptable data amount for the 2nd frame and equal to or larger than the limit data amount. As a result, the transmission controller 38*a* obtains the compressed image signal of the 2nd frame including the compressed in-vivo image $P_2$.

The transmission controller 38*a* estimates the non-receiving period immediately after the receiving period for the image signal of the 2nd frame based on the non-receiving period information of the 1st frame, like in the first embodiment described above. The transmission controller 38*a* then transmits the compressed image signal of the 2nd frame to the transmitting unit 14 and controls the transmitting unit 14 to wirelessly transmit the compressed image signal of the 2nd frame during the estimated non-receiving period (within the time interval $\Delta T_2$).

The non-receiving period immediately after the receiving period for the image signal of the 2nd frame corresponds to a non-transmitting period from when the capsule endoscope 2 ends transmitting the image signal (in-vivo image $P_2$) of the 2nd frame until when the capsule endoscope 2 starts transmission of the image signal (in-vivo image $P_3$) of the 3rd frame, as shown in FIG. 8. Therefore, the non-receiving period immediately after the receiving period for the image signal of the 2nd frame is shortened with increase in the frame rate of the image signals successively wirelessly transmitted by the capsule endoscope 2. The data amount controller 38*b* causes the data compressing unit 35 to compress (reduce) the data amount of the image signal of the 2nd frame into a data amount that can be wirelessly transmitted by the transmitting unit 14 during the non-receiving period of the receiving device 34, which is shortened with the increase in the frame rate. As a result, the transmission controller 38*a* can cause the transmitting unit 14 to wirelessly transmit the image signal of the 2nd frame compressed by the data compressing unit 35 during the shortened non-receiving period (that is, the non-receiving period immediately after the receiving period for the image signal of the 2nd frame) of the receiving device 34.

The compressed image signal of the 2nd frame wirelessly transmitted by the receiving device 34 during the non-receiving period is received by the viewer 7, like the compressed image signal of the 1st frame. The signal processing unit 22 of the viewer 7 performs the predetermined expansion (decompression), image processing, and the like for the compressed image signal of the 2nd frame to generate the in-vivo image $P_2$ of the subject 1, and displays the generated in-vivo image $P_2$ in real time.

Meanwhile, when the acceptable data amount for the 2nd frame is smaller than the limit data amount, the data amount controller 38*b* determines the in-vivo image $P_2$ in the amount equal to or smaller than the acceptable data amount for the 2nd frame is ineffective. In this case, the data amount controller 38*b* controls the data compressing unit 35 to compress the image signal of the 2nd frame (that is, the in-vivo image $P_2$) into the limit data amount, instead of the acceptable data amount for the 2nd frame. As a result, the transmission controller 38*a* obtains the limit compressed image signal of the 2nd frame including the in-vivo image $P_2$ compressed into the limit data amount.

The limit compressed image signal of the 2nd frame exceeds the acceptable data amount capable of being wirelessly transmitted during the non-receiving period immediately after the receiving period for the image signal of the 2nd frame (the acceptable data amount for the 2nd frame), and thus cannot be wirelessly transmitted during the non-receiving period by the transmitting unit 14. Accordingly, the transmission controller 38*a* segments the limit compressed image signal of the 2nd frame to be wirelessly transmitted during plural non-receiving periods by the transmitting unit 14.

Figure 9:
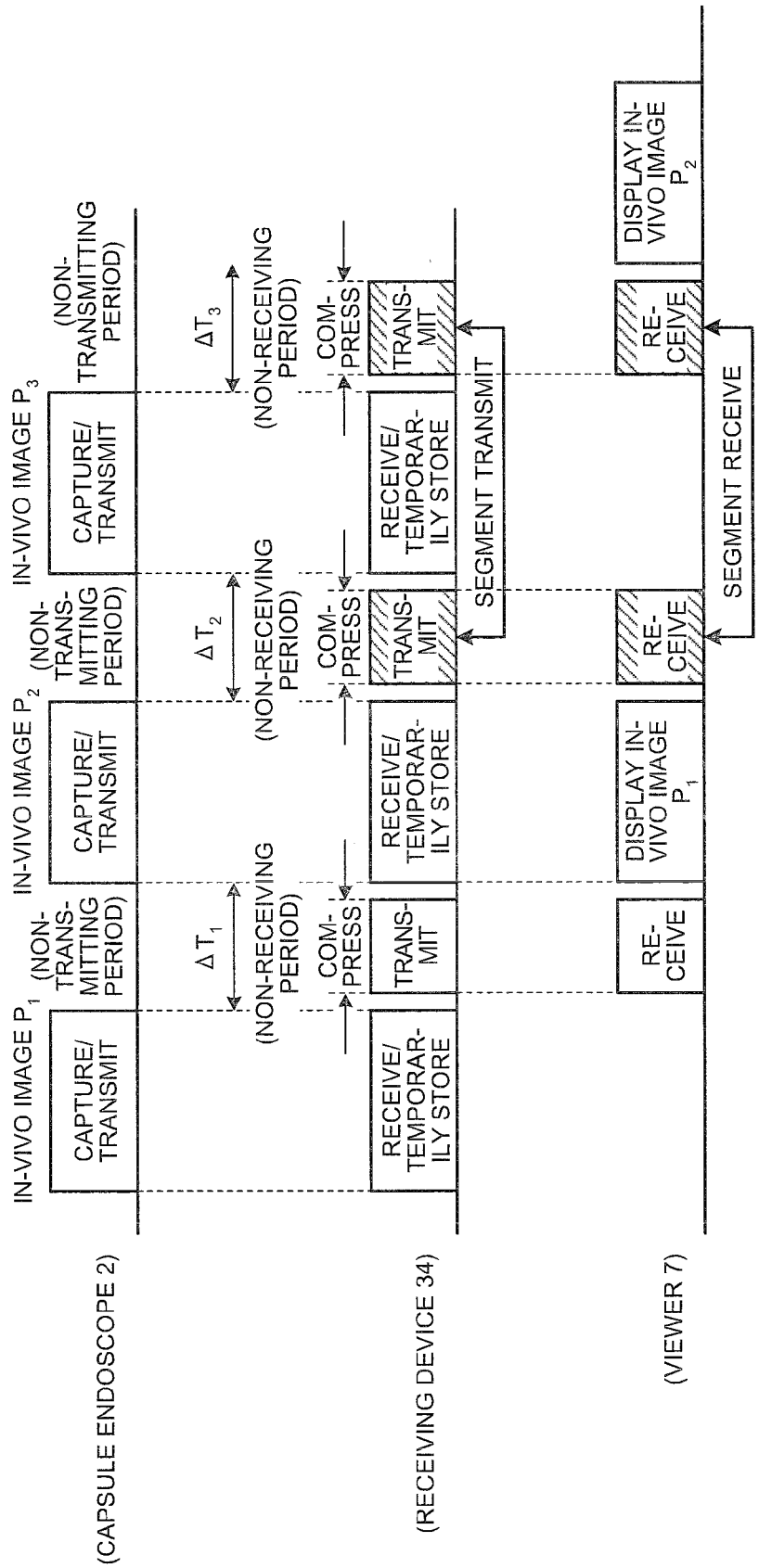
FIG. 9 is a schematic diagram of an example of a sequential control in the receiving device that wirelessly transmits a compressed image signal to the viewer during a plurality of non-receiving periods by segmenting the signal.

Specifically, as shown in FIG. 9, the transmission controller 38*a* causes the transmitting unit 14 to wirelessly transmit a part of the limit compressed image signal of the 2nd frame during the non-receiving period immediately after the receiving period for the image signal of the 2nd frame. The transmission controller 38*a* then causes the transmitting unit 14 to wirelessly transmit a remaining part of the limit compressed image signal of the 2nd frame during a non-receiving period after the non-receiving period for the 2nd frame, that is, a non-receiving period immediately after a receiving period for the image signal of the 3rd frame.

The limit compressed image signal of the 2nd frame segmented and wirelessly transmitted during the plural non-receiving periods is received by the viewer 7, like the compressed image signal of the 2nd frame. The signal processing unit 22 of the viewer 7 performs the predetermined expansion (decompression), the image processing, and the like for the limit compressed image signal of the 2nd frame to generate the in-vivo image $P_2$ of the subject 1, and displays the generated in-vivo image $P_2$ in real time.

The receiving device 34 including the transmission controller 38*a* and the data amount controller 38*b* successively compresses the image signals of the 3rd and subsequent frames, which are successively received from the capsule endoscope 2, depending on the non-receiving periods, and successively wirelessly transmits to the viewer 7, the compressed image signals or limit compressed image signals of the 3rd and subsequent frames during the non-receiving period immediately after the receiving period, or during the plural non-receiving periods by segmenting the signal, like the image signal of the 2nd frame. The viewer 7 successively generates the in-vivo images $P_3, \ldots,$ and $P_n$ of the 3rd and subsequent frames received from the receiving device 34, and successively displays the generated in-vivo images $P_3, \ldots,$ and $P_n$ in real time, like the compressed image signal or limit compressed image signal of the 2nd frame.

As described above, in the second embodiment of the present invention, the receiving device is configured to have the same function and configuration as those of the first embodiment described above. The receiving device is also configured to calculate the acceptable data amount of the image signal capable of being wirelessly transmitted during the non-receiving period immediately after the receiving period in which the image signal from the in-vivo-image acquiring device such as the capsule endoscope is received, compress the image signal into an amount equal to or smaller than the calculated acceptable data amount, and wirelessly transmit the compressed image signal during the non-receiving period. Accordingly, even when the non-receiving period for the image signal from the in-vivo-image acquiring device is shortened with the increase in the frame rate of the image signals successively wirelessly transmitted by the in-vivo-image acquiring device, the compression rate for the image signal can be increased with the shortening of the non-received period to generate a compressed image signal that can be wirelessly transmitted during the shortened non-receiving period. As a result, the same effect as that of the first embodiment described above can be achieved, and the receiving device that can wirelessly transmit the image signal from the in-vivo-image acquiring device in real time during the non-receiving period for the image signal shortened with the increase in the frame rate of the in-vivo-image acquiring device can be realized.

Further, the limit data amount which is the minimum data amount of the image signal capable of including an effective in-vivo image, and the acceptable data amount that can be wirelessly transmitted during the non-receiving period are compared with each other. When the acceptable data amount is equal to or larger than the limit data amount, the image signal is compressed into an amount equal to or smaller than the acceptable data amount (and equal to or larger than the limit data amount). When the acceptable data amount is smaller than the limit data amount, the image signal is compressed into the limit data amount. Therefore, the image signal including an effective in-vivo image can be reliably wirelessly transmitted during the non-receiving period immediately after the receiving period or during plural non-receiving periods by segmenting the signal.

Third Embodiment

A third embodiment of the present invention is explained next. In the second embodiment described above, the wireless-transmission-target image signal to be wirelessly transmitted during the non-receiving period is compressed to reduce the data amount of the wireless-transmission-target image signal. In the third embodiment, pixels of the wireless-transmission-target image signal are thinned out to reduce the data amount of the wireless-transmission-target image signal.

Figure 10:
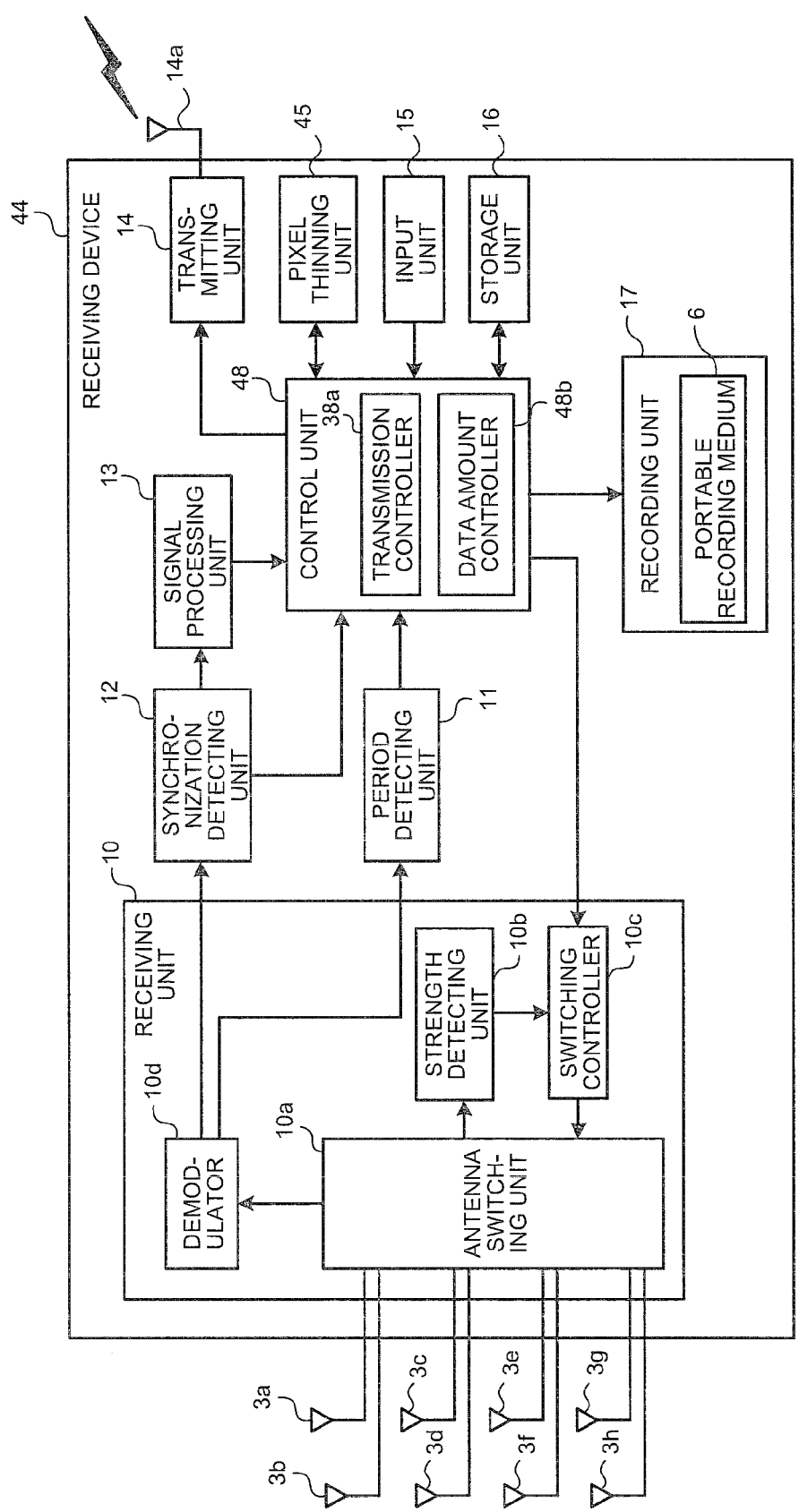
FIG. 10 is a schematic block diagram of a configuration example of a receiving device according to a third embodiment of the present invention.

FIG. 10 is a schematic block diagram of a configuration example of a receiving device according to the third embodiment of the present invention. As shown in FIG. 10, a receiving device 44 according to the third embodiment includes a pixel thinning unit 45 instead of the data compressing unit 35 of the receiving device 34 according to the second embodiment described above, and includes a control unit 48 instead of the control unit 38. Configurations other than these units are the same as those of the second embodiment, and the same constituent elements as those of the second embodiment are denoted by the same reference numerals. An in-vivo-image acquiring system according to the third embodiment includes the receiving device 44 instead of the receiving device 34 of the in-vivo-image acquiring system according to the second embodiment described above.

The pixel thinning unit 45 serves as a data reducing unit that thins out pixels in the wireless-transmission-target image signal which is to be wirelessly transmitted by the transmitting unit 14 to the external viewer 7, to reduce the data amount of the wireless-transmission-target image signal. Specifically, the pixel thinning unit 45 obtains the image signal in frame unit outputted by the synchronization detecting unit 12 through the control unit 48, and thins out pixels of the image data in the obtained image signal (that is, the in-vivo image of the subject 1) under control of the control unit 48. The pixel thinning unit 45 can change a pixel thinning ratio for the image data under control of the control unit 48. The pixel thinning unit 45 performs the pixel thinning for the image data in the wireless-transmission-target image signal based on the pixel thinning ratio instructed by the control unit 48, and transmits the image signal subjected to the pixel thinning to the control unit 48.

The control unit 48 is realized using a CPU that executes processing programs, a ROM that has the processing programs and the like previously stored therein, and a RAM that stores therein operation parameters and the like. The control unit 48 controls the constituent units of the receiving device 44 and controls input and output of signals between the constituent units. In this example, the control unit 48 controls the receiving unit 10, the period detecting unit 11, the synchronization detecting unit 12, the signal processing unit 13, the transmitting unit 14, the input unit 15, the storage unit 16, and the recording unit 17, like the control unit 38 of the receiving device 34 according to the second embodiment described above. The control unit 48 obtains the non-receiving period information detected by the period detecting unit 11, the image signal in frame unit outputted by the synchronization detecting unit 12, and the in-vivo image generated and outputted by the signal processing unit 13.

The control unit 48 includes a data amount controller 48b instead of the data amount controller 38b of the receiving device 34 according to the second embodiment described above, and the transmission controller 38a. The transmission controller 38a in the receiving device 44 according to the third embodiment has a transmission control function to cause the transmitting unit 14 to wirelessly transmit the image signal subjected to the pixel thinning by the pixel thinning unit 45, instead of the image signal compressed by the data compressing unit 35, during a non-receiving period immediately after a receiving period of the receiving device 44 or during plural non-receiving periods by segmenting the image signal. The remaining functions of the transmission controller 38a are the same as those in the second embodiment described above.

The data amount controller 48b controls the pixel thinning unit 45 to control the data amount of the wireless-transmission-target image signal. Specifically, the data amount controller 48b calculates an acceptable data amount in the non-receiving period immediately after the receiving period of the receiving device 44. The data amount controller 48b determines a pixel thinning ratio for image data in the image signal based on the calculated acceptable data amount, and controls the pixel thinning unit 45 to perform the pixel thinning for the image data (that is, the in-vivo image) in the image signal according to the determined pixel thinning ratio. The data amount controller 48b controls the pixel thinning unit 45 to reduce the wireless-transmission-target image signal to an amount equal to or smaller than the acceptable data amount.

The data amount controller 48b determines whether the in-vivo image in the image signal subjected to the pixel thinning by the pixel thinning unit 45 to have the amount equal to or smaller than the acceptable data amount is effective. The data amount controller 48b has the minimum data amount (limit data amount) of the image signal capable of including (keeping) an effective in-vivo image previously set, and compares the limit data amount and the acceptable data amount with each other. When the acceptable data amount is equal to or larger than the limit data amount as a result of the comparison, the data amount controller 48*b* determines the in-vivo image in the image signal subjected to the pixel thinning to have the amount equal to or smaller than the acceptable data amount (hereinafter, also "in-vivo image in the amount equal to or smaller than the acceptable data amount") is effective. The data amount controller 48*b* controls the pixel thinning unit 45 to perform the pixel thinning for the image data in the image signal to have an amount equal to or smaller than the acceptable data amount and equal to or larger than the limit data amount. When the acceptable data amount is smaller than the limit data amount, the data amount controller 48*b* determines the in-vivo image in the amount equal to or smaller than the acceptable data amount is invalid. In this case, the data amount controller 48*b* controls the pixel thinning unit 45 to perform the pixel thinning for the image data in the image signal to have the limit data amount.

The control unit 48 including the transmission controller 38*a* and the data amount controller 48*b* repeatedly performs an approximately same process procedure as that from Steps S201 to S210 (see FIG. 7). The control unit 48 thereby temporally separates the receiving period for the image signal from the capsule endoscope 2 and the transmitting period for the image signal to the viewer 7, and performs the pixel thinning for the image signal from the capsule endoscope 2 depending on the non-receiving period immediately after the receiving period, to control the transmitting unit 14 to successively wirelessly transmit the image signals successively subjected to the pixel thinning to the viewer 7 according to time series.

In this example, at Step S206, the data amount controller 48*b* determines a pixel thinning ratio that enables to reduce the image signal to the data amount in the range equal to or smaller than the acceptable data amount and equal to or larger than the limit data amount, and causes the pixel thinning unit 45 to perform the pixel thinning for the wireless-transmission-target image signal based on the determined pixel thinning ratio, instead of compressing the wireless-transmission-target image signal. When the acceptable data amount is equal to or larger than the limit data amount, the data amount controller 48*b* can determine the pixel thinning ratio that enables to reduce the image signal to the acceptable data amount equal to or larger than the limit data amount, and cause the pixel thinning unit 45 to perform the pixel thinning for the wireless-transmission-target image signal based on the determined pixel thinning ratio. When the original data amount of the image signal from the capsule endoscope 2 is equal to or smaller than the acceptable data amount, the data amount controller 48*b* does not cause the pixel thinning unit 45 to reduce the image signal.

At Step S208, the data amount controller 48*b* determines a pixel thinning ratio that enables to reduce the wireless-transmission-target image signal to the limit data amount and causes the pixel thinning unit 45 to perform the pixel thinning based on the determined pixel thinning ratio, instead of compressing the wireless-transmission-target image signal. In this case, the data amount controller 48*b* can reduce the wireless-transmission-target image signal to the limit data amount.

Figure 11:
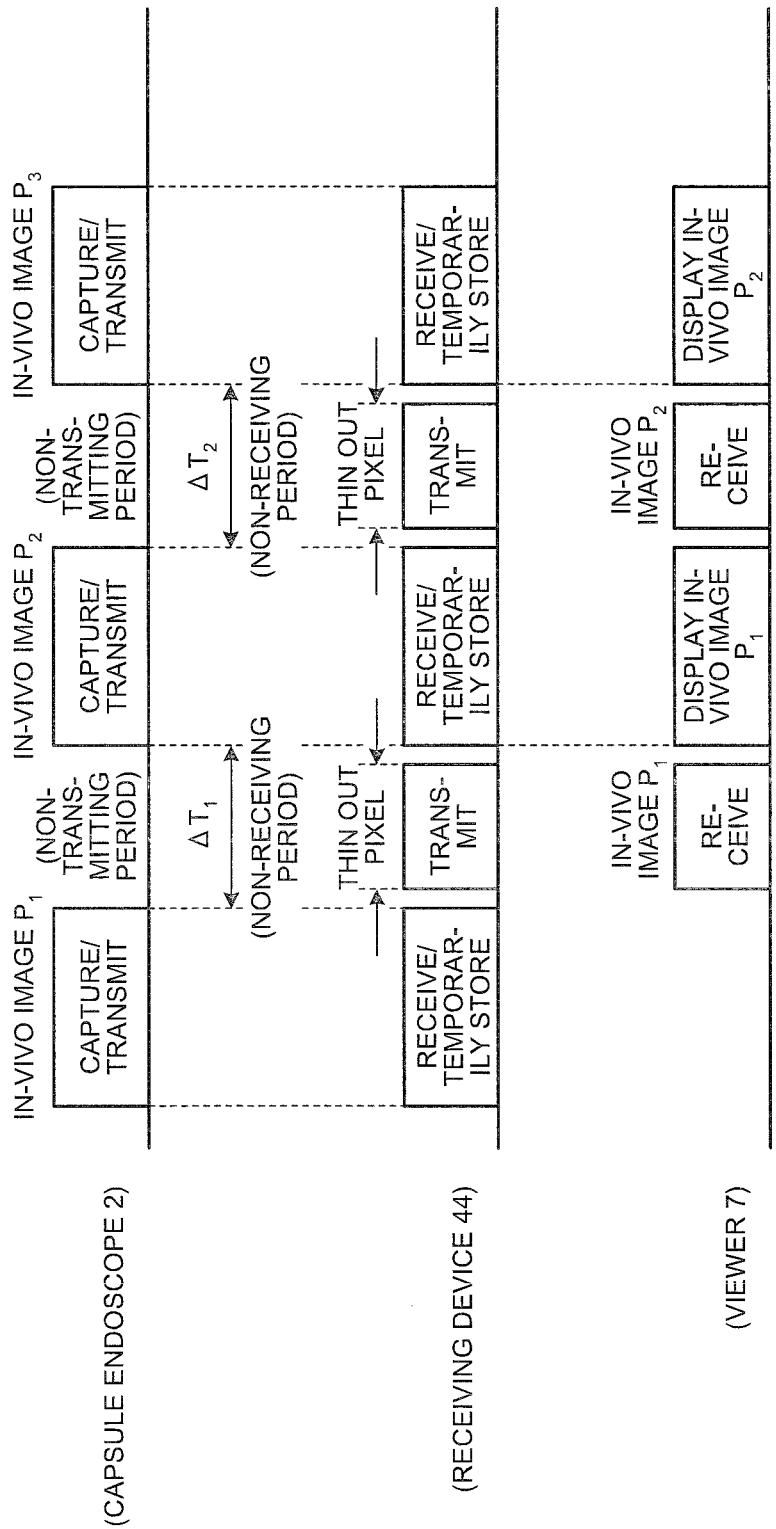
FIG. 11 is a schematic diagram of an example of a sequential control in a receiving device that wirelessly transmits an image signal already subjected to pixel thinning, to a viewer during a non-receiving period of the receiving device.

An operation of the data amount controller 48*b* is specifically explained using an example in which the receiving device 44 receives the image signals of 1st to 3rd frames from the capsule endoscope 2 within the subject 1. FIG. 11 is a schematic diagram of an example of a sequential control in the receiving device 44 that wirelessly transmits the image signal already subjected to the pixel thinning, to the viewer 7 during the non-receiving period of the receiving device 44.

As shown in FIG. 11, when the capsule endoscope 2 within the subject 1 captures the in-vivo image $P_1$ of the 1st frame and wirelessly transmits the image signal of the 1st frame including the in-vivo image $P_1$, the receiving device 44 receives the image signal of the 1st frame from the capsule endoscope 2 and temporarily stores therein the received image signal of the 1st frame. The receiving device 44 performs the pixel thinning for the image signal of the 1st frame depending on the non-receiving period immediately after the receiving period for the image signal of the 1st frame, and wirelessly transmits the image signal of the 1st frame already subjected to the pixel thinning to the viewer 7 during the non-receiving period.

In the receiving device 44, the data amount controller 48*b* calculates an acceptable data amount for the 1st frame that can be wirelessly transmitted during the estimated non-receiving period (within the default time interval $\Delta T_1$) immediately after the receiving period for the image signal of the 1st frame, and determines whether the in-vivo image $P_1$ in an amount equal to or smaller than the acceptable data amount for the 1st frame is effective, like the data amount controller 38*b* of the receiving device 34 according to the second embodiment described above. When the acceptable data amount for the 1st frame is equal to or larger than the limit data amount, the data amount controller 48*b* determines the in-vivo image $P_1$ in the amount equal to or smaller than the acceptable data amount for the 1st frame is effective, and controls the pixel thinning unit 45 to perform the pixel thinning for the in-vivo image $P_1$ in the image signal of the 1st frame to have an amount equal to or smaller than the acceptable data amount for the 1st frame and equal to or larger than the limit data amount.

Meanwhile, when the capsule endoscope 2 captures the in-vivo image $P_2$ of the 2nd frame and wirelessly transmits the image signal of the 2nd frame including the in-vivo image $P_2$, the receiving device 44 receives the image signal of the 2nd frame from the capsule endoscope 2 and temporarily stores therein the receiving image signal of the 2nd frame. The receiving device 44 performs the pixel thinning for the image signal of the 2nd frame depending on the non-receiving period immediately after the receiving period for the image signal of the 2nd frame, and wirelessly transmits the image signal of the 2nd frame already subjected to the pixel thinning, to the viewer 7 during the non-receiving period.

In the receiving device 44, like the data amount controller 38*b* of the receiving device 34 according to the second embodiment described above, the data amount controller 48*b* calculates an acceptable data amount for the 2nd frame that can be wirelessly transmitted during the estimated non-receiving period (within the time interval $\Delta T_2$) immediately after the receiving period for the image signal of the 2nd frame. The data amount controller 48*b* then determines whether the in-vivo image $P_2$ in an amount equal to or smaller than the acceptable data amount for the 2nd frame is effective. When the acceptable data amount for the 2nd frame is equal to or larger than the limit data amount, the data amount controller 48*b* determines the in-vivo image $P_2$ in the amount equal to or smaller than the acceptable data amount for the 2nd frame is effective, and controls the pixel thinning unit 45 to perform the pixel thinning for the in-vivo image $P_2$ in the image signal of the 2nd frame to have an amount equal to or smaller than the acceptable data amount for the 2nd frame and equal to or larger than the limit data amount.

As described above, the non-receiving period immediately after the receiving period for each image signal is shortened with increase in the frame rate of the image signals successively wirelessly transmitted by the capsule endoscope 2. The data amount controller 48b causes the pixel thinning unit 45 to perform the pixel thinning (that is, reduction) of image data of each image signal to obtain a data amount that can be wirelessly transmitted by the transmitting unit 14 during the non-receiving period of the receiving device 44, which is shortened with the increase in the frame rate. As a result, the transmission controller 38a can cause the transmitting unit 14 to successively wirelessly transmit the image signals successively subjected to the pixel thinning by the pixel thinning unit 45, during the respective shortened non-receiving periods of the receiving device 44 (for example, during respective non-receiving periods shown in FIG. 11).

Meanwhile, when the acceptable data amount for the 2nd frame is smaller than the limit data amount, the data amount controller 48b determines the in-vivo image $P_2$ in the amount equal to or the smaller than the acceptable data amount for the 2nd frame is invalid. In this case, the data amount controller 48b controls the pixel thinning unit 45 to perform the pixel thinning of the image signal of the 2nd frame (that is, the in-vivo image $P_2$) to have the limit data amount, instead of the acceptable data amount for the 2nd frame.

Because the image signal of the 2nd frame subjected to the pixel thinning to have the limit data amount exceeds the acceptable data amount that can be wirelessly transmitted during the non-receiving period immediately after the receiving period for the image signal of the 2nd frame (acceptable data amount for the 2nd frame), the image signal of the 2nd frame is segmented to be wirelessly transmitted by the transmitting unit 14 during plural non-receiving periods, like in the second embodiment described above.

The data amount controller 48b having the control function as described above causes the pixel thinning unit 45 to successively perform the pixel thinning also for the image signals of the 3rd and subsequent frames based on the pixel thinning ratio corresponding to the respective non-receiving period, like the image signal of the 2nd frame.

As described above, in the third embodiment of the present invention, the pixel thinning ratio for the image data is determined depending on the non-receiving period for the image signal, and the wireless-transmission-target image signal is subjected to the pixel thinning based on the determined pixel thinning ratio, instead of being compressed as in the second embodiment described above, so that the image signal subjected to the pixel thinning is wirelessly transmitted. In other points, the third embodiment is configured in the same manner as that of the second embodiment described above. Therefore, the third embodiment achieves the same effect as that of the second embodiment, and can realize the receiving device that can reduce the image signal by the pixel thinning for the image data, without reducing the image signal by the compression of the image data.

Fourth Embodiment

A fourth embodiment of the present invention is explained next. In the second and third embodiments described above, the image signal having the data amount reduced by the image compression or the pixel thinning is wirelessly transmitted during the non-receiving period of the receiving device, which is shortened with the increase in the frame rate of the image signals from the capsule endoscope 2. In the fourth embodiment, a wireless transmission rate for the image signals is increased depending on the non-receiving period of the receiving device, and the wireless-transmission-target image signal is wirelessly transmitted at the increased rate during the non-receiving period of the receiving device, which is shortened with the increase in the frame rate of the image signals.

Figure 12:
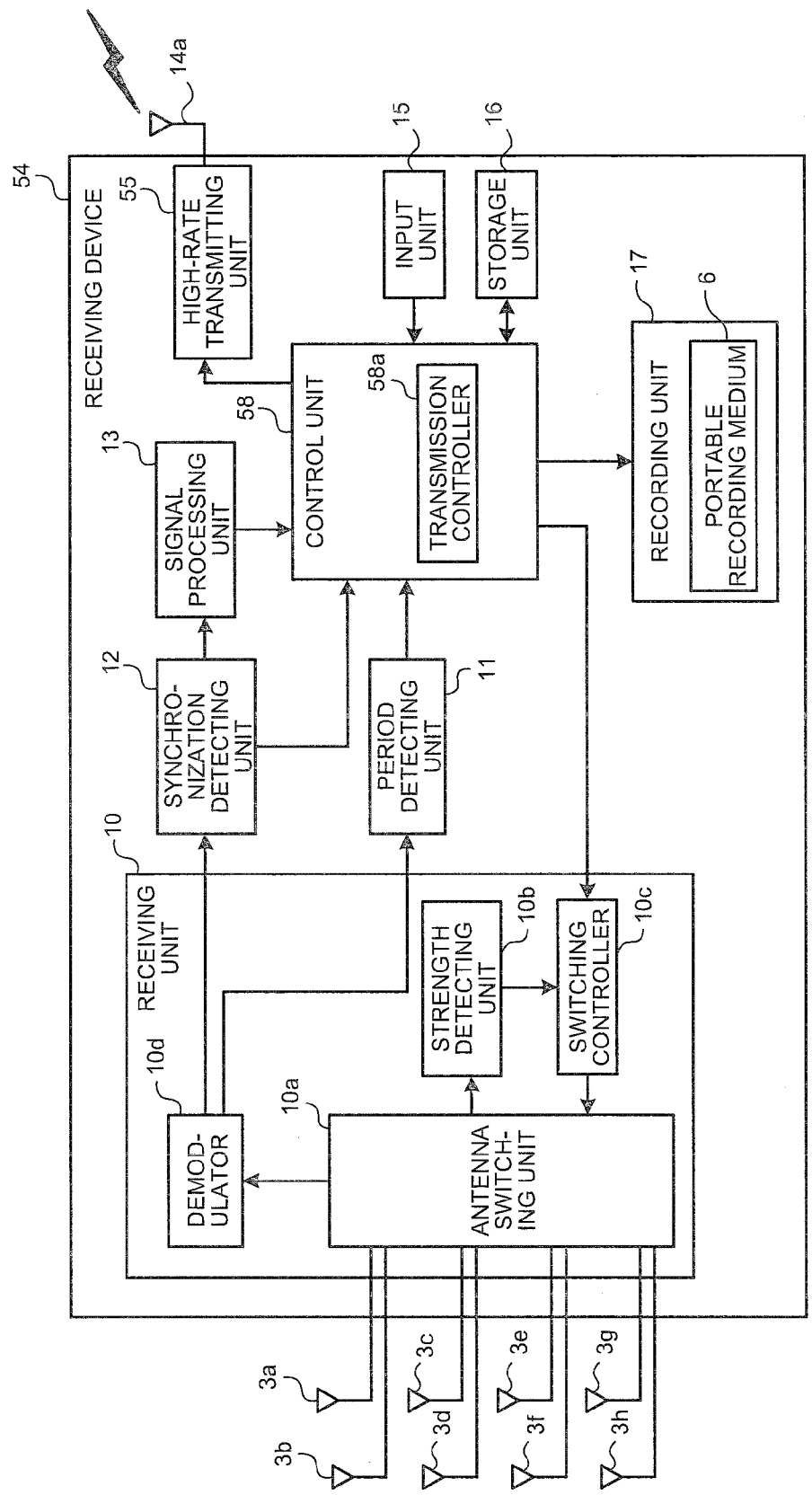
FIG. 12 is a schematic block diagram of a configuration example of a receiving device according to a fourth embodiment of the present invention.

FIG. 12 is a schematic block diagram of a configuration example of a receiving device according to the fourth embodiment of the present invention. As shown in FIG. 12, a receiving device 54 according to the fourth embodiment includes a high-rate transmitting unit 55 instead of the transmitting unit 14 of the receiving device 4 according to the first embodiment described above, and a control unit 58 instead of the control unit 18. Configurations other than these units are the same as those of the first embodiment, and like constituent elements are denoted by like reference numerals. An in-vivo-image acquiring system according to the fourth embodiment of the present invention includes the receiving device 54 instead of the receiving device 4 of the in-vivo-image acquiring system according to the first embodiment described above (see FIG. 1).

The high-rate transmitting unit 55 has the similar function to that of the transmitting unit 14 of the receiving device 4 according to the first embodiment described above. The high-rate transmitting unit 55 further has a high-rate wireless-transmitting function to wirelessly transmit the image signal from the capsule endoscope 2 at a transmission rate increased under control of the control unit 58 during a non-receiving period of the receiving device 54. Specifically, the high-rate transmitting unit 55 obtains the image signal in frame unit (image signal from the capsule endoscope 2) under the control of the control unit 58, and performs modulation or the like for the obtained image signal in frame unit to generate a wireless signal corresponding to the image signal in frame unit. The high-rate transmitting unit 55 wirelessly transmits the wireless signal (that is, the image signal from the capsule endoscope 2) to the viewer 7 via the transmitting antenna 14a at a high rate during the non-receiving period immediately after the receiving period for the image signal from the capsule endoscope 2. The high-rate transmitting unit 55 increases the transmission rate for the wireless-transmission-target image signal by increasing a transmission frequency for the wireless-transmission-target image signal or modulating the wireless-transmission-target image signal using a modulation method suitable for high-rate wireless transmission (for example, multilevel modulation method), or by combining the increase in the transmission frequency and the modulation, under the control of the control unit 58.

The control unit 58 is realized by a CPU that executes processing programs, a ROM that has the processing programs and the like previously stored therein, and a RAM that stores therein operation parameters and the like. The control unit 58 controls the constituent units of the receiving device 54 and controls input and output of signals between the constituent units. In this example, the control unit 58 controls the receiving unit 10, the period detecting unit 11, the synchronization detecting unit 12, the signal processing unit 13, the input unit 15, the storage unit 16, and the recording unit 17, like the control unit 18 of the receiving device 4 according to the first embodiment described above. The control unit 58 obtains the non-receiving period information detected by the period detecting unit 11, the image signal in frame unit outputted by the synchronization detecting unit 12, and the in-vivo image generated and outputted by the signal processing unit 13.

The control unit 58 includes a transmission controller 58a instead of the transmission controller 18a of the receiving device 4 according to the first embodiment described above. The transmission controller 58a controls the high-rate transmitting unit 55 to wirelessly transmit the image signal from the capsule endoscope 2, which is obtained from the synchronization detecting unit 12, during the non-receiving period immediately after the receiving period for the image signal. Specifically, the transmission controller 58a estimates the non-receiving period immediately after the receiving period for the image signal based on the non-receiving period information obtained from the period detecting unit 11 and the obtaining timing for the non-receiving period information, and calculates a transmission rate sufficient to wirelessly transmit the image signal during the estimated non-receiving period. The transmission controller 58a controls the high-rate transmitting unit 55 to wirelessly transmit the image signal at the calculated transmission rate. In this example, the transmission controller 58a causes the high-rate transmitting unit 55 to increase the transmission frequency of the wireless-transmission-target image signal, or to perform modulation of the wireless-transmission-target image signal according to the modulation method suitable for the high-rate wireless transmission, such as the multilevel modulation method, or to perform a combination of the increase in the transmission frequency and the modulation. By controlling at least one of the transmission frequency and the modulation method of the high-rate transmitting unit 55, the transmission controller 58a increases the transmission rate for the image signal to an extent where the image signal can be wirelessly transmitted during the non-receiving period immediately after the receiving period, and causes the high-rate transmitting unit 55 to wirelessly transmit the wireless-transmission-target image signal at the increased transmission rate (high-rate wireless transmission).

An operation of the receiving device 54 according to the fourth embodiment of the present invention is explained next. FIG. 13 is a flowchart of an example of a process procedure performed by the control unit 58 of the receiving device 54 according to the fourth embodiment. The receiving device 54 receives the image signal wirelessly transmitted by the capsule endoscope 2, as in the first embodiment described above. The control unit 58 calculates the transmission rate for the image signal from the capsule endoscope 2 depending on the non-receiving period immediately after the receiving period for the image signal from the capsule endoscope 2, and controls the high-rate transmitting unit 55 to wirelessly transmit the image signal from the capsule endoscope 2 at a high rate based on the calculated wireless-transmission rate to the viewer 7 during the non-receiving period.

That is, as shown in FIG. 13, the control unit 58 obtains the image signal from the capsule endoscope 2 within the subject 1 (Step S301), and temporarily stores the obtained image signal in the storage unit 16 (Step S302), like at Steps S101 and 5102. The control unit 58 then determines whether it is currently the receiving period for the image signal (Step S303) like at Step S103. When it is during the receiving period for the image signal (YES at Step S303), the control unit 58 returns to Step S301 and repeats the process procedure from Step S301. The control unit 58 repeatedly performs the processes from Steps S301 to S303 until the receiving period for the image signal ends, so that the image signal in frame unit is completely obtained from the synchronization detecting unit 12, and the image signal in frame unit is temporarily stored in the storage unit 16. In this example, the control unit 58 stores the obtained image signal of the nth frame and the non-receiving period information of the (n-1)th frame associated with each other in the storage unit 16, and keeps and manages the image signal of the nth frame and the non-receiving period information of the (n-1)th frame to be read as necessary.

Meanwhile, when it is determined at Step S303 that it is currently not the receiving period for the image signal (NO at Step S303), the control unit 58 calculates a transmission rate sufficient to wirelessly transmit the image signal during the non-receiving period immediately after the receiving period (Step S304). At Step S304, the transmission controller 58a estimates the non-receiving period immediately after the receiving period for the image signal of the nth frame based on the non-receiving period information of the (n-1)th frame obtained from the period detecting unit 11 and the obtaining timing for the non-receiving period information of the (n-1)th frame. The transmission controller 58a then calculates a transmission rate for the image signal of the nth frame at which the image signal can be wirelessly transmitted by the high-rate transmitting unit 55 during the non-receiving period, based on the time interval $\Delta T_n$, which is the length or the estimated non-receiving period, and a data amount of the image signal of the nth frame.

The control unit 58 then controls the high-rate transmitting unit 55 to rapidly wirelessly transmit the wireless-transmission-target image signal at the transmission rate calculated at Step S304 during the non-receiving period immediately after the receiving period (Step S305). At Step S305, the transmission controller 58a causes the high-rate transmitting unit 55 to increase the transmission frequency of the image signal of the nth frame, or to modulate the image signal of the nth frame according to the modulation method suitable for the high-rate wireless transmission, such as the multilevel modulation method, or to perform a combination of the increase in the transmission frequency and the modulation. By controlling at least one of the transmission frequency and the modulation method of the high-rate transmitting unit 55, the transmission controller 58a controls (increases) the transmission rate for the wireless transmission to be performed by the high-rate transmitting unit 55 to a level similar the transmission rate calculated at Step S304. The transmission controller 58a then causes the high-rate transmitting unit 55 to rapidly wirelessly transmit the image signal of the nth frame at the increased transmission rate (that is, the transmission rate calculated at Step S304). As a result, the image signal of the nth frame wirelessly transmitted at a high rate is received by the viewer 7 during the non-receiving period immediately after the receiving period for the image signal of the nth frame of the receiving device 54.

When the wireless-transmission-target image signal can be fully wirelessly transmitted during the non-receiving period immediately after the receiving period without increasing the transmission rate, the transmission controller 58a causes the high-rate transmitting unit 55 to wirelessly transmit the wireless-transmission-target image signal during the non-receiving period immediately after the receiving period at a predetermined transmission rate, for example the transmission rate calculated at Step S304, in approximately the same manner as at Step S104 (that is, without increasing the transmission rate of the high-rate transmitting unit 55).

The control unit 58 then determines whether to complete the process (Step S306), like at Step S105. When the process is not completed (NO at Step S306), the control unit 58 returns to Step S301 and repeats the process procedure from Step S301. On the other hand, when it is determined that the process has been completed (YES at Step S306), the control unit 58 ends the process.

An operation of the transmission controller 58a that performs the control to increase the transmission rate for the image signal from the capsule endoscope 2 according to the shortened non-receiving period and wirelessly transmit the image signal to the viewer 7 during the shortened receiving period based on the increased transmission rate is specifically explained next, using the image signals of 1st to 3rd frames received from the capsule endoscope 2 within the subject 1 as an example. FIG. 14 is a schematic diagram of an example of a sequential control in the receiving device 54 that wirelessly transmits the image signal to the viewer 7 based on the transmission rate increased according to the shortened non-receiving period of the receiving device 54.

As shown in FIG. 14, when the capsule endoscope 2 within the subject 1 captures the in-vivo image $P_1$ of the 1st frame and wirelessly transmits the image signal of the 1st frame including the in-vivo image $P_1$, the receiving device 54 receives the image signal of the 1st frame from the capsule endoscope 2 and temporarily stores therein the received image signal of the 1st frame. The receiving device 54 calculates a transmission rate for the image signal according to the non-receiving period immediately after the receiving period for the image signal of the 1st frame. The receiving device 54 then wirelessly transmits the image signal of the 1st frame to the viewer 7 at the calculated transmission rate during the non-receiving period.

In the receiving device 54, the transmission controller 58a estimates the non-receiving period immediately after the receiving period for the image signal of the 1st frame based on the default time interval $\Delta T_1$ obtained from the period detecting unit 11 and the obtaining timing for the default time interval $\Delta T_1$. The transmission controller 58a calculates a transmission rate V1 sufficient to wirelessly transmit the image signal of the 1st frame during the non-receiving period immediately after the receiving period for the image signal of the 1st frame, based on the default time interval $\Delta T_1$, which is the length of the estimated non-receiving period, and a data amount of the image signal of the 1st frame (that is, data amount of the in-vivo image $P_1$).

The non-receiving period immediately after the receiving period for the image signal of the 1st frame is shortened with increase in the frame rate of the image signals successively wirelessly transmitted by the capsule endoscope 2, as described above. The transmission controller 58a increases the transmission rate of the high-rate transmitting unit 55 up to the transmission rate V1 sufficient to wirelessly transmit the image signal during the non-receiving period of the receiving device 54, which is shortened with the increase in the frame rate. The transmission controller 58a transmits the image signal of the 1st frame to the high-rate transmitting unit 55, and controls the high-rate transmitting unit 55 to wirelessly transmit the image signal of the 1st frame at the transmission rate V1 during the non-receiving period of the default time interval $\Delta T_1$. As a result, the transmission controller 58a can cause the high-rate transmitting unit 55 to wirelessly transmit the image signal of the 1st frame during the shortened non-receiving period of the receiving device 54 (that is, during the non-receiving period immediately after the receiving period for the image signal of the 1st frame).

The image signal of the 1st frame wirelessly transmitted at a high rate by the receiving device 54 during the non-receiving period is received by the viewer 7. The viewer 7 displays the in-vivo image $P_1$ of the subject 1 in real time based on the image signal of the 1st frame, as in the first embodiment described above.

Meanwhile, when the capsule endoscope 2 captures the in-vivo image $P_2$ of the 2nd frame and wirelessly transmits the image signal of the 2nd frame including the in-vivo image $P_2$, the receiving device 54 receives the image signal of the 2nd frame from the capsule endoscope 2 and temporarily stores therein the received image signal of the 2nd frame. The receiving device 54 calculates a transmission rate for the image signal according to the non-receiving period immediately after the receiving period for the image signal of the 2nd frame, and wirelessly transmits the image signal of the 2nd frame to the viewer 7 at the calculated transmission rate during the non-receiving period.

In the receiving device 54, the transmission controller 58a estimates the non-receiving period immediately after the receiving period for the image signal of the 2nd frame based on the non-receiving period information of the 1st frame detected by the period detecting unit 11 and the obtaining timing for the non-receiving period information. The transmission controller 58a calculates a transmission rate V2 sufficient to wirelessly transmit the image signal of the 2nd frame during the non-receiving period immediately after the receiving period for the image signal of the 2nd frame, based on the time interval $\Delta T_2$, which is the length of the estimated non-receiving period, and a data amount of the image signal of the 2nd frame (that is, data amount of the in-vivo image $P_2$).

The non-receiving period immediately after the receiving period for the image signal of the 2nd frame is shortened with increase in the frame rate of the image signals successively wirelessly transmitted by the capsule endoscope 2, as described above. The transmission controller 58a increases the transmission rate of the high-rate transmitting unit 55 up to the transmission rate V2 sufficient to wirelessly transmit the image signal during the non-receiving period of the receiving device 54, which is shortened with the increase in the frame rate. The transmission controller 58a transmits the image signal of the 2nd frame to the high-rate transmitting unit 55, and controls the high-rate transmitting unit 55 to wirelessly transmit the image signal of the 2nd frame at the transmission rate V2 during the non-receiving period of the time interval $\Delta T_2$. As a result, the transmission controller 58a can cause the high-rate transmitting unit 55 to wirelessly transmit the image signal of the 2nd frame during the shortened non-receiving period of the receiving device 54 (that is, during the non-receiving period immediately after the receiving period for the image signal of the 2nd frame).

The image signal of the 2nd frame wirelessly transmitted at a high rate by the receiving device 54 during the non-receiving period is received by the viewer 7. The viewer 7 displays the in-vivo image $P_2$ of the subject 1 in real time based on the image signal of the 2nd frame, like in the case of the image signal of the 1st frame.

The receiving device 54 including the transmission controller 58a also successively wirelessly transmits the image signals of the 3rd and subsequent frames successively received from the capsule endoscope 2, to the viewer 7 based on the transmission rates properly increased according to the corresponding non-receiving periods, like the image signal of the 2nd frame. The viewer 7 successively generates the in-vivo images $P_3, \ldots, P_n$ of the 3rd and subsequent frames received from the receiving device 54 and successively displays in real time the generated in-vivo images $P_3, \ldots, P_n$, like in the case of the image signal of the 2nd frame.

As described above, the receiving device according to the fourth embodiment of the present invention is configured to have the same function and configuration as those of the first embodiment described above. Further, the receiving device is configured to increase the transmission rate for the image signal by controlling at least one of increasing in the transmission frequency for the image signal and the modulation method (for example, multilevel modulation method) depending on the non-receiving period immediately after the receiving period in which the image signal from the in-vivo-image acquiring device such as the capsule endoscope is received, and to wirelessly transmit the image signal at the increased transmission rate during the non-receiving period. Accordingly, even when the non-receiving period for the image signal from the in-vivo-image acquiring device is shortened with the increase in the frame rate of the image signals successively wirelessly transmitted by the in-vivo-image acquiring device, the transmission rate for the image signal can be increased up to the transmission rate sufficient for wireless transmission during the shortened non-receiving period, without reducing the data amount of the in-vivo image in the image signal (that is, without deteriorating the in-vivo image). As a result, the same effect as that of the first embodiment described above is achieved, and the receiving device that can wirelessly transmit the image signal from the in-vivo-image acquiring device in real time during the non-receiving period for the image signal shortened with the increase in the frame rate by the in-vivo-image acquiring device, without deteriorating the in-vivo image in the image signal, can be realized.

In the first to fourth embodiments of the present invention, the group of in-vivo images of the subject 1 is stored in the portable recording medium 6 attached to the receiving device. However, the present invention is not limited thereto, and it is possible that the portable recording medium 6 is removably attached to the viewer 7 and the group of in-vivo images of the subject 1 is stored in the portable recording medium 6 in the viewer 7. It is also possible that a recording medium such as a hard disk is provided in the viewer 7 without using the portable recording medium 6 and the group of in-vivo images of the subject 1 is stored in the recording medium of the viewer 7. In this case, the viewer 7 serves as the real-time display device that successively displays the in-vivo images of the subject 1 in real time, and also serves as a recording medium that transfers data between the receiving device that receives the image signals from the capsule endoscope 2 and the image display device 5.

In the second and third embodiments of the present invention, the image signal reduced to the limit data amount is segmented to be wirelessly transmitted during plural non-receiving periods. However, the present invention is not limited thereto, and a segment data amount of the image signal segmented to be wirelessly transmitted during the plural non-receiving periods can be a segment data amount obtained by segmenting the image signal reduced to the acceptable data amount into plural pieces, or can be a segment data amount obtained by segmenting the image signal in an original data amount before reduction into plural pieces.

Furthermore, in the second and third embodiments of the present invention, an example in which the image signal is segmented into two pieces and wirelessly transmitted during the non-receiving period immediately after the receiving period and the next non-receiving period has been described. However, the present invention is not limited thereto, and the image signal can be segmented into plural pieces and wirelessly transmitted during the non-receiving period immediately after the receiving period and one or more non-receiving periods following the non-receiving period.

In the fourth embodiment of the present invention, the image signal is wirelessly transmitted based on the transmission rate increased depending on the non-receiving period immediately after the receiving period. However, the present invention is not limited thereto, and it is possible to increase the transmission rate for the image signal depending on the non-receiving period immediately after the receiving period and further reduce a data amount of the image signal depending on the non-receiving period. That is, the second or third embodiment described above and the fourth embodiment can be properly combined. In this case, it is necessary that the receiving device 54 according to the fourth embodiment described above include the data compressing unit 35 and the data amount controller 38*b* described in the second embodiment, or the pixel thinning unit 45 and the data amount controller 48*b* described in the third embodiment.

Furthermore, in the first to fourth embodiments of the present invention, the capsule endoscope including the imaging function to capture the in-vivo images and the wireless transmitting function to wirelessly transmit the in-vivo images in the capsule-shaped casing has been described as an example of the in-vivo-image acquiring device. However, the present invention is not limited thereto, and the in-vivo-image acquiring device that wirelessly transmits the image signals to the receiving device according to the present invention can be a capsule medical apparatus including the imaging function to capture in-vivo images and the wireless transmitting function to wirelessly transmit the in-vivo image to a receiving device outside a subject.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A receiving device comprising:
   a receiving unit that receives, via a receiving antenna, a first image signal in a first receiving period and a second image signal in a second receiving period, each of the first image signal and second image signal including an in-vivo image of a subject that is captured by an in-vivo-image acquiring device introduced into the subject;
   a transmitting unit that wirelessly transmits the first image signal and the second image signal to a real-time display device that displays the in-vivo image included in the first image signal and the in-vivo image included in the second image signal in real time;
   a detecting unit that detects a length of a first non-receiving period in which the receiving unit does not receive any image signal, the first non-receiving period being immediately after the first receiving period and immediately before the second receiving period; and
   a control unit that estimates, based on the length of the first non-receiving period detected by the detecting unit, a length of a second non-receiving period in which the receiving unit does not receive any image signal, the second non-receiving period being immediately after the second receiving period, and performs a control, based on the estimated length of the second non-receiving period, to cause the transmitting unit to wirelessly transmit the second image signal to the real-time display device during the second non-receiving period.

2. The receiving device according to claim 1, further comprising a data reducing unit that reduces a data amount of the image signal to be wirelessly transmitted to the real-time display device, wherein
the control unit calculates a data amount that can be wirelessly transmitted by the transmitting unit during the non-receiving period, and performs a control to reduce the image signal to an amount equal to or smaller than the calculated data amount.

3. The receiving device according to claim 2, wherein the control unit determines whether the in-vivo image included in the image signal having a reduced data amount equal to or smaller than the calculated data amount is effective, and performs a control to wirelessly transmit the image signal having the reduced data amount equal to or smaller than the calculated data amount when the in-vivo image is determined to be effective, while performing a control to wirelessly transmit the image signal in a data amount capable of including an effective in-vivo image by segmenting the signal to be wirelessly transmitted during a plurality of the non-receiving periods when the in-vivo image is determined to be ineffective.

4. The receiving device according to claim 3, wherein when the in-vivo image included in the image signal having the reduced data amount equal to or smaller than the calculated data amount is determined to be ineffective, the control unit performs a control to reduce the image signal to a minimum data amount capable of including an effective in-vivo image and to wirelessly transmit the image signal reduced to the minimum data amount by segmenting the signal to be wirelessly transmitted during the plural non-receiving periods.

5. The receiving device according to claim 2, wherein the data reducing unit is a compressing unit that compresses the image signal.

6. The receiving device according to claim 2, wherein the data reducing unit is a pixel thinning unit that performs pixel thinning for the in-vivo image included in the image signal.

7. The receiving device according to claim 1, wherein the control unit calculates a transmission rate sufficient to wirelessly transmit the image signal during the non-receiving period and performs a control to wirelessly transmit the image signal at the calculated transmission rate.

8. The receiving device according to claim 7, wherein the control unit controls at least one of a modulation method and a transmission frequency of the transmitting unit and causes the transmitting unit to wirelessly transmit the image signal at the calculated transmission rate.

* * * * *